(12) United States Patent
Meyer et al.

(10) Patent No.: US 10,266,819 B2
(45) Date of Patent: Apr. 23, 2019

(54) ROBUST, EASY TO USE IMMOBILIZED ENZYME REACTORS

(71) Applicant: PERFINITY BIOSCIENCES, Inc., West Lafayette, IN (US)

(72) Inventors: Kevin Wayne Meyer, West Lafayette, IN (US); John Patrick O'Grady, Lafayette, IN (US); Robert Harold Ellis, Half Moon Bay, CA (US); Nicholas Brian Herold, West Lafayette, IN (US); Derrick Nathaniel Poe, West Lafayette, IN (US)

(73) Assignee: PERFINITY BIOSCIENCES, INC., West Lafayette, IN (US)

( * ) Notice: Subject to any disclaimer, the term of this patent is extended or adjusted under 35 U.S.C. 154(b) by 23 days.

(21) Appl. No.: 14/763,441

(22) PCT Filed: Jan. 30, 2014

(86) PCT No.: PCT/US2014/013782
§ 371 (c)(1),
(2) Date: Jul. 24, 2015

(87) PCT Pub. No.: WO2014/120890
PCT Pub. Date: Aug. 7, 2014

(65) Prior Publication Data
US 2015/0361415 A1    Dec. 17, 2015

Related U.S. Application Data

(60) Provisional application No. 61/908,214, filed on Nov. 25, 2013, provisional application No. 61/880,198, (Continued)

(51) Int. Cl.
*C12N 11/08* (2006.01)
*C12N 11/02* (2006.01)
(Continued)

(52) U.S. Cl.
CPC .............. *C12N 11/08* (2013.01); *C12M 21/18* (2013.01); *C12M 33/00* (2013.01); *C12M 45/20* (2013.01); *C12N 11/02* (2013.01); *C12N 11/14* (2013.01)

(58) Field of Classification Search
None
See application file for complete search history.

(56) References Cited

U.S. PATENT DOCUMENTS

| 5,094,819 A | 3/1992 | Yager et al. |
| 6,432,290 B1 | 8/2002 | Harrison et al. |
| 6,872,575 B2 | 3/2005 | Regnier |

FOREIGN PATENT DOCUMENTS

| WO | WO 2011/112188 | * | 9/2011 |
| WO | WO 2011/112188 A1 | | 9/2011 |

OTHER PUBLICATIONS

Hartmann, Chem. Mater. 17: 4577-4593 (2005).*
(Continued)

*Primary Examiner* — Erin M. Bowers
(74) *Attorney, Agent, or Firm* — Barnes & Thornburg LLP

(57) ABSTRACT

The disclosure provides an innovative immobilized enzyme reactor working system that includes improved reactor formats, heating element, optimum buffers, filtration apparatus and collection componentry for easy to use sample preparation. The system provides enhanced recovery, improved reproducibility and parallel processing capabilities capable of quantitatively processing hundreds of difficult to digest samples simultaneously in a shortened period of time.

36 Claims, 25 Drawing Sheets

$$E+S \underset{K_{-1}}{\overset{K_1}{\rightleftharpoons}} ES \overset{K_2}{\rightarrow} E+P$$

Substrate Binding | Catalytic Step

Related U.S. Application Data filed on Sep. 20, 2013, provisional application No. 61/873,907, filed on Sep. 5, 2013, provisional application No. 61/843,489, filed on Jul. 8, 2013, provisional application No. 61/807,525, filed on Apr. 2, 2013, provisional application No. 61/773,252, filed on Mar. 6, 2013, provisional application No. 61/758,797, filed on Jan. 31, 2013.

(51) Int. Cl.
  *C12N 11/14* (2006.01)
  *C12M 1/40* (2006.01)
  *C12M 1/26* (2006.01)
  *C12M 1/00* (2006.01)

(56) References Cited

OTHER PUBLICATIONS

Ekstrom et al., Anal. Chem. 72: 286-293 (2000).*
Murphy, "Chemical modification of bovine trypsin for use in peptide synthesis," dissertation, Dublin City University, 1996.*
Daglioglu et al., Artificial Cells, Blood Substitutes, and Biotechnology 40: 378-384 (2012).*
Sipos et al., Biochemistry 9(14): 2766-2775 (1970).*
Ekstrom, et al., Integrated Microanalytical Technology Enabling Rapid and Automated Protein Identification. Anal Chem Jan. 15, 2000, vol. 72 No. 2, pp. 286-292 (Especially p. 287 col. 2 para 2, 3, fig 1; p. 288, col. 1, para 3, 4; p. 290 para 2).
Ma et al., Immobilized Enzyme Reactors in Proteomics, Trends in Analytical Chemistry, May 2011, vol. 30, No. 5, pp. 691-702 (Especially p. 699 col. 1 para 3-5, entire article).
Sun et al., High Efficiency and Quantitatively Reproducible Protein Digestion by Trypsin-immobilized Magnetic Microspheres, J Chromatography A, Jan. 13, 2012, vol. 1220, pp. 68-74 (Especially p. 6 para 3, p. 12 fig 1A).
Pall Corporation, Polypropylene Membranes [online] 2012 [retrieved Mar. 31, 2014]. URL:http://www.pall.com/main/oem-materials-and-devices/printfriendly.page?lid=gri78lhg&industry=OEM-Materials-and-Devices&country—undefined (Espeically p. 3).
International Search Report and Written Opinion prepared for International Application No. PCT/US14/13782, dated Jun. 27, 2014.
Supelco Bulletin 910, "Guide to Solid Phase Extraction," published by Sigma Aldrich, 1998, 12 pages.
Tuli, L. et al., "LC-MS Based Detection of Differential Protein Expression," J. Proteomics Bioinform., 2009, 2, 416-438.
Calleri, E. et al., "New monolithic chromatographic supports for macromolecules immobilization: Challenges and opportunities," Journal of Pharmaceutical and Biomedical Analysis, 2012, 69, 64-76.
Jiang, H. et al., "A hydrophilic immobilized trypsin reactor with N-vinyl-2-pyrrolidinone modified polymer microparticles as matrix for highly efficient protein digestion with low peptide residue," J. Chromatography A, 2012, 1246, 111-116.
Jiang, B. et al., "Hydrophilic immobilized trypsin reactor with magnetic graphene oxide as support for high efficient proteome digestion," J. Chromatography A, 1254, 8-13.
Liang, Y. et al., "Hydrophilic monolith based immobilized enzyme reactors in capillary and on microchip for high-throughput proteomic analysis," Chromatography A, 1218, 2898-2905.

\* cited by examiner

Position 1

Position 2

ROBUST, EASY TO USE IMMOBILIZED ENZYME REACTORS

CROSS-REFERENCE TO RELATED APPLICATIONS

This application is a US National Phase filing of PCT/US2014/013782, filed on Jan. 30, 2014, which claims benefit of US provisional applications of U.S. 61/758,797, filed on Jan. 31, 2013, U.S. 61/773,252, filed on Mar. 6, 2013, U.S. 61/807,525, filed on Apr. 2, 2013, U.S. 61/843,489, filed on Jul. 8, 2013, U.S. 61/873,907, filed on Sep. 5, 2013, U.S. 61/880,198, filed on Sep. 20, 2013, and U.S. 61/908,214, filed on Nov. 25, 2013. All of the disclosures of which are hereby expressly incorporated by reference entirely.

FIELD OF INVENTION

This invention discloses an innovative immobilized enzyme reactor working system. Specifically, the immobilized enzyme reactor working system has improved immobilized enzyme, reactor formats, heating element, buffers, filtration apparatus and collection plate componentry for easy to use sample preparation. The system provides simplified as well as improved digestion, enhanced recovery, superior reproducibility and parallel processing capabilities for quantitatively processing hundreds of difficult to digest samples simultaneously in a shortened period of time.

BACKGROUND

The growing impact of proteins as efficacious drugs and diagnostic biomarkers is forcing the analytical community to deal with extremely high levels of analyte and sample complexity. However, due to the time and cost associated with developing an enzyme linked immunoassay (ELISA), mass spectrometric approaches are playing an increasing role in protein analyses. Furthermore, mass spectrometric methods enable detection of isoform variations and post-translational modifications; identification of these features being key to an understanding of protein function and activity.

Applications of enzymatic catalyses in biotechnology are often limited by the activity, stability and specificity of the enzyme under desired operating conditions. As such, the discovery and/or development of enzymes with improved characteristics can be the impetus for scientific breakthrough. Notably, *Thermus aquaticus* (Taq) polymerase has become one of the most important enzymes in molecular biology due to its ability to withstand the protein-denaturing conditions (high temperature) required during polymerase chain reaction (PCR) temperature cycling. Attempts to apply such enzymes to proteomics have resulted in restricted success. Thermolysin is an example of one such thermophilic enzyme applied to proteomics (Bark, et. al. J. Am. Chem. Soc. 2001, 123, 1774-1775). However, thermolysin cleaves hydrophobic amino acids and therefore lacks the specificity requisite for broad application. Alternatively trypsin is particularly well suited for mass spectrometric applications, since it has a very well defined specificity; it hydrolyzes only the peptide bonds in which the carbonyl group consists of either an arginine or lysine residue. However, many enzymes of homeothermic origin, including trypsin, have an optimal operating temperature of approximately 37° C. (Promega Technical Manual #9PIV511). As such, samples digested with these enzymes must be pretreated; proceeded by offline denaturation (e.g. guanidine, urea treatments), reduction (e.g. dithiothreitol, tris(2-carboxyethyl)phosphine treatments) and alkylation (e.g. n-ethylmaleimide, iodoacetamide, iodoacetic acid treatments). These steps are necessary for the exposure of cleavage sites existing within a protein's three dimensional structure. A thermostable form of trypsin, maintaining activity, stability and specificity at protein denaturing conditions would remove the need to perform these pretreatment steps.

In addition to a lack of thermal stability, another major limitation for many enzymes related to protein digestion pathways, including trypsin, is their low Kcat/Km ratio (catalytic efficiency). As such use of these enzymes is typically associated with hours-long incubation times. In and of itself, digestion is performed under kinetically unfavorable conditions. This phenomenon can be expressed using the Michaelis-Menten model (see FIG. 1). The drop in substrate concentration as a digestion nears completion makes it very difficult to obtain complete conversion to product. While enzymes typically produce product at an initial rate that is approximately linear for a short period after the start of the reaction, as the reaction proceeds and substrate is consumed, the rate continuously slows. The progression of substrate conversion to products can be represented as a process curve, as shown in FIG. 2. Using the digestion of a simple protein (e.g. insulin, see FIGS. 3 and 4) and a typical digestion protocol (50:1 protein:enzyme ratio, 37° C.) as an example it is easy to replicate this phenomenon in-situ. Incomplete trypsin digestion can lead to underestimations of protein concentrations. Furthermore, if some samples are more difficult to digest than others, for example plasma samples varying in protein content, an incomplete digestion would result in irreproducibility.

An enzyme working system that would eliminate the need to perform sample pretreatment while enabling a complete and reproducible digestion of protein samples is desired.

SUMMARY OF THE INVENTION

This disclosure provides an immobilized enzyme reactor (IMER) preserving optimum enzyme thermal stability and activity at protein denaturing conditions. The IMER comprises essentially the following components:
  a. at least one enzyme; and
  b. an extended hydrophilic polymer coating immobilizing the enzyme to a supporting material. The extended hydrophilic polymer is:
    sized to be precluded from the interior structure of the enzyme; and
    making at least one hydrophilic modification to the enzyme's exterior residues.

In some preferred embodiment, the aforementioned IMER's enzyme interior is made more hydrophobic through the use of a hydrophobic modifier sized to penetrate the enzyme and making at least one modification to said enzyme's interior residue.

In some preferred embodiment the aforementioned protein denaturing condition is an elevated temperature at or above 37° C.

This disclosure also provides an IMER that is configured to have enhanced digestion, recovery and reproducibility. The IMER comprising:
  at least one immobilized enzyme placed in at least one reaction vessel, the reaction vessel has uniform heat conduction;
  a heating apparatus to provide uniform heat to the reaction vessel; and a device or means separating the immobilized enzyme from the enzyme's reaction product to obtain compatibility with downstream product analyses.

In some preferred embodiment the aforementioned heating apparatus is a heating block, column oven, multichannel heater, Polymerase Chain Reaction thermo cycler, water bath, oven, microwave oven or any combination of above.

This disclosure also provides an IMER preserving optimum enzyme thermal stability and activity at protein denaturing conditions. The IMER is configured to undergo uniform heating and/or agitating as desired, and comprises essentially the following components:

at least one immobilized enzyme placed in at least one reaction vessel. The reaction vessel has uniform heat conduction;

a heating apparatus to provide uniform heat and agitation to the reaction vessel;

a device or means separating the immobilized enzyme from the enzyme's reaction product to obtain compatibility with downstream product analyses;

an extended hydrophilic polymer coating immobilizing the enzyme to a supporting material. The extended hydrophilic polymer is:

sized to be precluded from the interior structure of the enzyme; and making at least one hydrophilic modification to the enzyme's exterior residues.

In some preferred embodiment, the aforementioned enzyme's interior is made more hydrophobic through the use of a hydrophobic modifier. The hydrophobic modifier is sized to penetrate the enzyme and making at least one modification to the enzyme's interior residue.

In some preferred embodiment, the aforementioned uniform agitation is in the form of rotation, end over end mixing, the use of a stir bar, sonicating (ultrasound), repeat pipetting or any combination of above.

In some preferred embodiment, the aforementioned uniform agitation is set to at least 10 rpm.

In some preferred embodiment, the aforementioned reactor format is a combination heater/shaker instrument, a heating block on a shaker, shaking in a convection oven, shaking in a water bath, shaking in a microwave over on any combination of above.

In some preferred embodiment, the aforementioned reaction vessel and heating apparatus are operated under static heating/shaking conditions.

In some preferred embodiment, the aforementioned reaction vessel and heating apparatus are operated under dynamic heating/shaking conditions.

In some preferred embodiment, the aforementioned reaction vessel is a thin walled PCR tube, any thin walled sample tube, or multi-well plate.

In some preferred embodiment, the aforementioned device uses a liquid permeable barrier. The barrier is sized to enable the passage of sample solutions and preclude the passage of the immobilized enzyme.

In some preferred embodiment, the aforementioned liquid permeable barrier utilizes hydrophilic membranes for increased recovery.

In some preferred embodiment, the aforementioned IMER further comprises blocking material in the reaction vessel. The blocking material is selected from the group consisting of bovine serum albumin, casein, fish gelatin, sugars, surfactants, chaotropes, detergents and salts.

In some preferred embodiment, the aforementioned reaction vessel is maintained at a controlled temperature compartment oven between 0° C. and 105'C.

In some preferred embodiment, the aforementioned IMER is a form of column, eppendorf tube, pipette tip, multi well plate, or magnetic bead.

In some preferred embodiment, the aforementioned IMER contains reaction buffer that is further comprised of organic solvents, chaotropes, surfactants, detergents, sugars, salts or any combination of above.

In some preferred embodiment, the aforementioned enzyme is selected from the group consisting of trypsin, chymotrypsin, Lys-C, Glu-C, Arg-C, Asp N, papain, pepsin, elastase, IdeS, pronase and PNGase F or a combination of above.

In some preferred embodiment, the aforementioned supporting material is selected from the group consisting of polystyrene, polystyrene/divinylbenzene, silica, controlled porosity glass, dextrans, agarose, acrylates and nitrocellulose.

In some preferred embodiment, the aforementioned supporting material is in a form of particle, monolithic, membrane, planar or microfluidic channel.

In some preferred embodiment, the aforementioned support material containing a magnetic core for sample handling in robotic devices.

In some preferred embodiment, the aforementioned enzyme's substrate is treated by reductive alkylation either before or after digestion.

This disclosure provides an improved IMER system, the system comprising essentially the following:

at least one immobilized enzyme coupled by an extended hydrophilic polymer coating on a supporting material; and at least one substrate in a uniformly heated reaction vessel. The reaction vessel contains a reaction buffer having a metal concentration greater than 1 millimolar, and the immobilized enzyme has accelerated reaction to the sample and enhanced recovery compared to a metal free reaction buffer.

In some preferred embodiment, the aforementioned the metal cation in the reaction buffer is selected from the group consisting of aluminum, calcium, copper, iron, magnesium, manganese, mercury, sodium and silver.

This disclosure provides an improved enzyme reactor system. The system comprising essentially the following:

at least one modified enzyme and at least one substrate. The ratio of the enzyme to the substrate is controlled above the traditional 1:50, preferably at a ratio exceeding 1:20;

a uniformly heated reaction vessel to encompass the enzyme and the substrate, wherein the reaction vessel contains a reaction buffer having a metal concentration greater than 1 millimolar, and wherein the enzyme has accelerated reaction to the substrate and enhanced recovery compared to a metal free reaction buffer.

This disclosure provides a method of producing enhanced protein recovery and reproducibility on enzyme reaction, comprising. The method includes the steps of:

providing at least one modified enzyme and one protein sample in at least one reaction vessel, wherein the reaction vessel has uniform heat conduction;

providing uniform heat to the reaction vessel;

separating the modified enzyme from the enzyme's reaction product; and analyzing the reaction product in a downstream compatible apparatus.

This disclosure provides a process of making an enzyme reactor, wherein the enzyme reactor preserving optimum enzyme thermal stability and activity at protein denaturing conditions. The process comprising the following steps:

a. first providing an enzyme, and an extended hydrophilic polymer coating, wherein the hydrophilic polymer coating is sized to be precluded from said enzyme's interior structure and making at least one hydrophilic modification on the enzyme's exterior residues;
b. second providing a hydrophobic modifier, the hydrophobic modifier is sized to penetrate the enzyme to make at least one modification on the enzyme's interior residues;

This disclosure provides a process of making an IMER, wherein the IMER preserving optimum enzyme thermal stability and activity at protein denaturing conditions. The process comprising the following steps:
a. first providing an enzyme, and an extended hydrophilic polymer coating immobilizing the enzyme to a form of support material, wherein the hydrophilic polymer coating is sized to be precluded from the enzyme's interior structure and making at least one hydrophilic modification on the enzyme's exterior residues;
b. second providing a hydrophobic modifier, the hydrophobic modifier is sized to penetrate the enzyme to make at least one modification on the enzyme's interior residues;
c. subjecting the product in step a and b to nitrogen analysis to an effective protein/resin ratio of at least 2.6 mg nitrogen/gram resin.

In some preferred embodiment, the aforementioned enzyme is selected from the group consisting of trypsin, chymotrypsin, Lys-C, Glu-C, Arg-C, Asp N, papain, pepsin, elastase, IdeS, pronase and PNGase F or a combination of above.

This disclosure provides an automated system for protein digestion, recovery and analysis. The system comprising at least an auto-sampler, an IMER with optimum enzyme thermal stability at protein denaturing conditions, a desalting column, and a reverse phase chromatography (RPC) column, wherein said IMER is made from the following process:
a. first providing an enzyme, and an extended hydrophilic polymer coating immobilizing said enzyme to a form of support material, wherein said hydrophilic polymer coating is sized to be precluded from said enzyme's interior structure and making at least one hydrophilic modification on said enzyme's exterior residues;
b. second providing a hydrophobic modifier, said hydrophobic modifier is sized to penetrate said enzyme to make at least one modification on said enzyme's interior residues;
c. subjecting the product in step a and b to nitrogen analysis to an effective protein/resin ratio of about 16% nitrogen content This disclosure provides an automated system for protein digestion, recovery and analysis. The system comprising at least a multichannel pipette, an IMER with optimum enzyme thermal stability at protein denaturing conditions, wherein the IMER is made from the following process:
a. first providing an enzyme, and an extended hydrophilic polymer coating immobilizing the enzyme to a form of support material, wherein the hydrophilic polymer coating is sized to be precluded from the enzyme's interior structure and making at least one hydrophilic modification on the enzyme's exterior residues;
b. second providing a hydrophobic modifier, the hydrophobic modifier is sized to penetrate the enzyme to make at least one modification on the enzyme's interior residues; and
c. subjecting the product in step a and b to nitrogen analysis to an effective protein/resin ratio of about 16% nitrogen content.

In some preferred embodiment, the aforementioned automated systems' IMER is maintained at a controlled temperature compartment oven between 0° C. and 105° C.

In some preferred embodiment, the aforementioned IMER is used to react with a substrate without alkylation and reduction process.

In some preferred embodiment, the aforementioned automated systems are used for disulfide bond mapping, peptide mapping, protein qualification or protein quantification.

These and other features, aspects and advantages of the present invention will become better understood with reference to the following figures, associated descriptions and claims.

DETAILED DESCRIPTION

Figure 1:
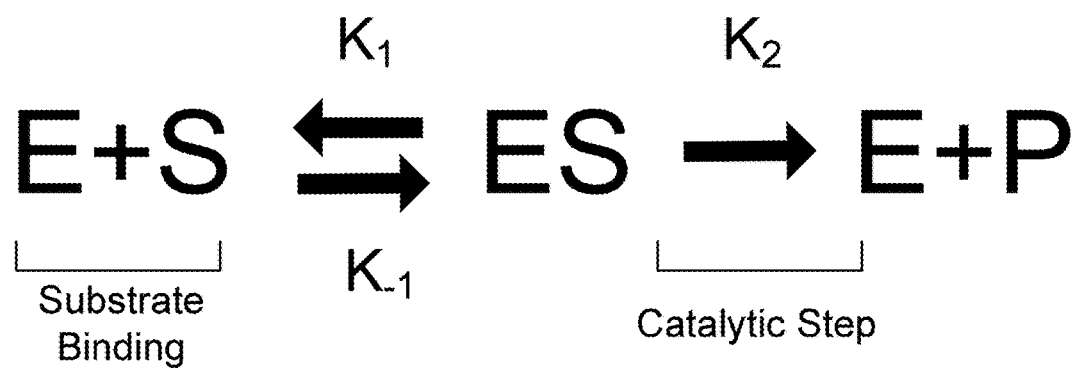
FIG. 1: Schematic representation of enzyme kinetics.
Figure 2:
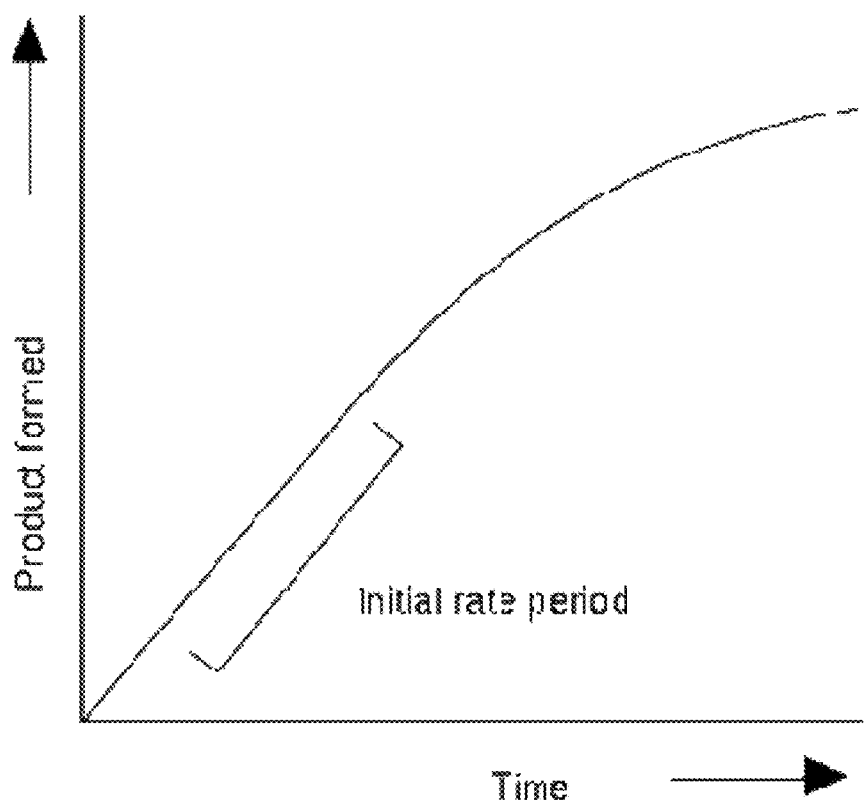
FIG. 2: Example of a progress curve for an enzyme reaction.

Disclosed herein is an immobilized enzyme reactor (IMER) comprising of the immobilized enzyme, reaction vessel and the reaction apparatus (e.g. heating apparatus). Ideally, the immobilization process enables the stabilization of the enzyme that is used under conditions such as extreme pH or temperature, and the IMER format enables rapid uniform digestion and can be used in conjunction with both quantitative and qualitative analyses.

The immobilization of trypsin has been described at length (Hsieh et al. 1996. Analytical Chemistry 68:455-462; Nadler et al. 1996. Journal of Chromatography A, 743:91-98; Freije et al. 2005. Journal of Proteome Research 4:1805-1813) but these immobilization only approaches fail to enable enzyme stability under denaturing conditions. In fact, Kumakura et al. (1984. Journal of Molecular Catalysis 23:1-8) showed that in the best case scenario, trypsin that was simply immobilized using multi-site modification exhibited a 60% reduction in activity after 30 minutes at 70° C. Marques et al. (2011. Biotechnology Progress 27:677-683) used an increase in rigidity as a means of establishing operation at 50° C. but this approach shows a lack of stability at further elevated temperatures (e.g. 70° C.) such that no attempts to operate at these temperatures were made. The stabilization of trypsin via hydropholization has been described (Mozhaev et al. 1988. European Journal of Biochemistry 173147-154 and Venkatesh and Sundaram 1998. Protein Engineering 11:691-698). However, with these strategies trypsin is unstable at 56.5° C. with activity being reduced to as little as 10% in 2 hours. Alteration of charge within the binding pocket by means of chemical modification has been documented by Freije (Freije et al. 2005. Journal of Proteome Research 4:1805-1813). However, this modification also fails to enable enzyme stability under denaturing conditions. In short, use of immobilization, enhanced, rigidity, hydrophilization and charge modification have all failed to provide an enzyme suitable for preparing samplers for mass spectrometric analysis with requisite activity, stability and specificity at denaturing conditions.

An enzyme working system that would eliminate the need to perform sample pretreatment while enabling a complete and reproducible digestion of protein samples is desired. In this description these features are obtained by means of immobilization of the enzyme using a large hydrophilic polymer sized enabling hydrophilization of the exterior of the protein while precluding hydrophilization of the interior of the enzyme. This step is followed by hydrophobic interior modification. It is important that a complete hydrophilization of the exterior of the protein precedes any hydrophobic modifications so as to prevent as destabilization of the exterior of the protein. This immobilization strategy is used in conjunction with non-obvious buffer compositions. The sample, enzyme and buffers are combined then digestion occurs using vessels with ideal heat transfer properties and heating devices with ideal uniformity. Preliminary results from exemplary protein analysis in this disclosure show the strategy consistently produced an immobilized enzyme reactor that preserves optimum enzyme thermal stability and activity at extreme temperatures. In addition, the high temperature immobilized enzyme reactor eliminated the necessity of substrate treatment such as alkylation and reduction, as well as reduced the reaction time to as short as seconds, providing compelling evidence that the disclosure herein provides a competitive edge over any other traditional in solution enzyme reactions or immobilization formulations.

Figure 6:
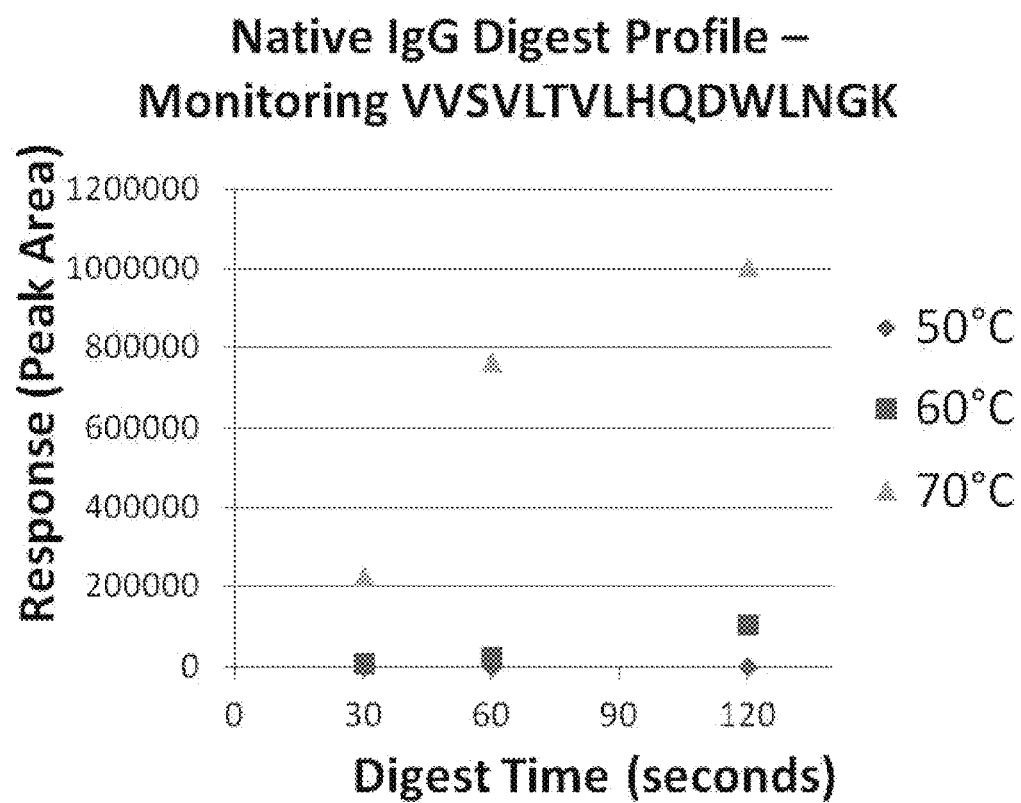
FIG. 6: Digestion of human $IgG_1$ at various times and temperatures using the immobilized enzyme prepared according to Example 2, packed in a column prepared according to Example 3 and processed using the automated system described in Example 4.
Figure 8:
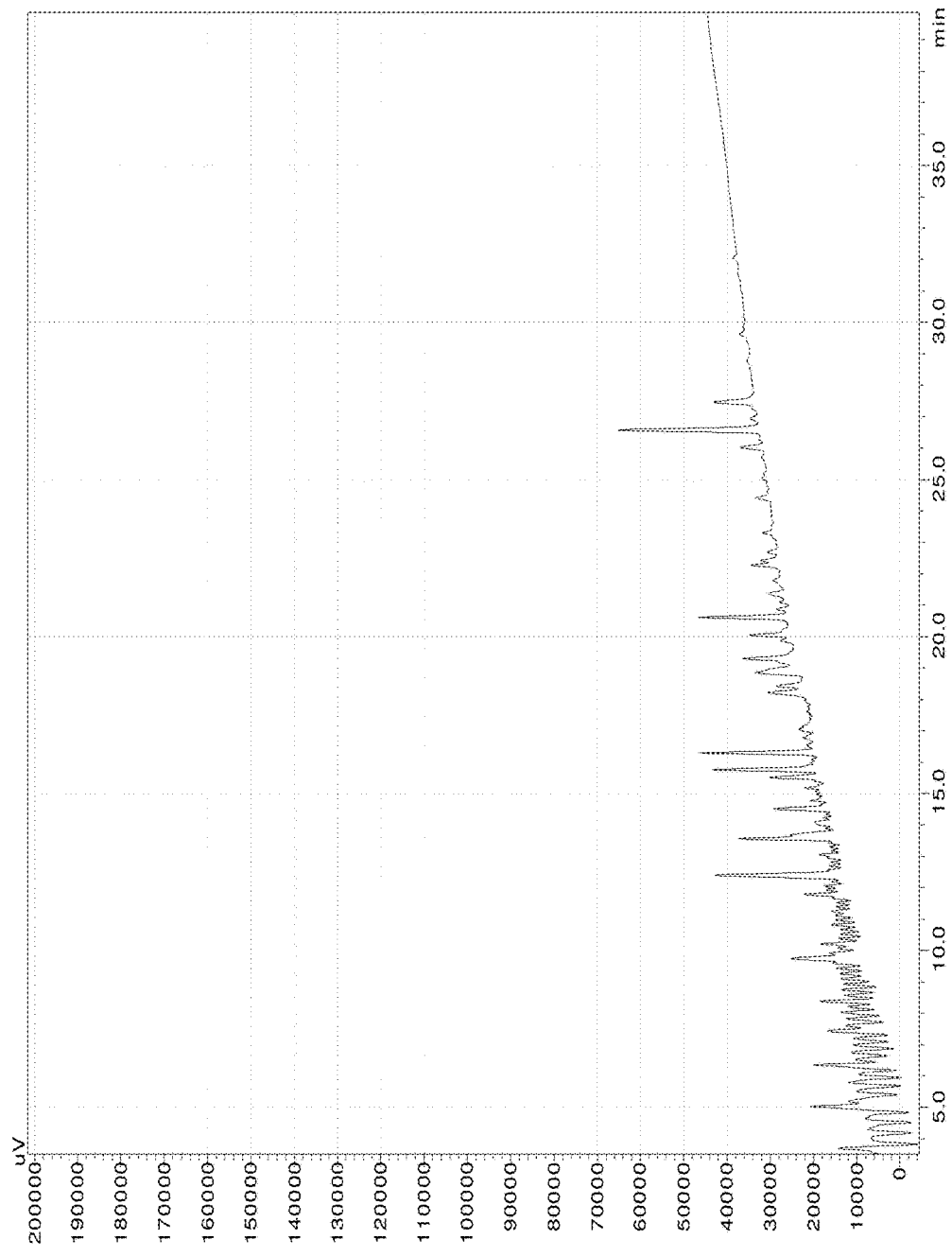
FIG. 8: Human IgG1 is digested using a single reaction mixture, no undigested materials are observed.
Figure 11:
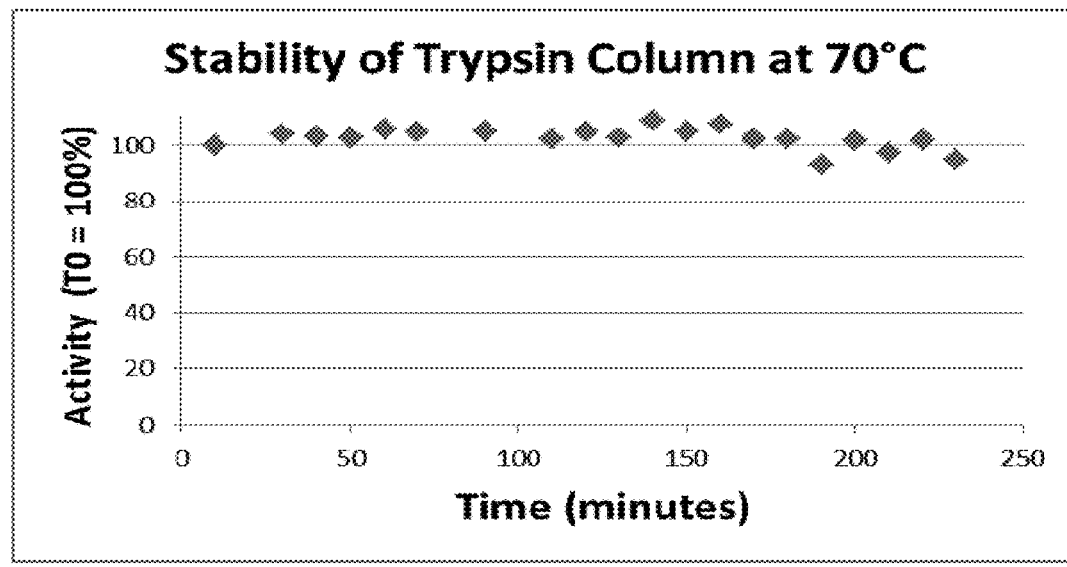
FIG. 11: Data showing sustained activity at 70° C. Immobilized enzyme prepared according to Example 2, packed in a column prepared according to Example 3 and samples processed using the automated system described in Example 4.

Without wishing to be limited by theory, it is believed that the operation and stability of enzymes at elevated temperatures is critical if denaturation and digestion are to be simultaneous. Given the diversity of proteins, the temperature at which proteins denature is sure to vary widely. However, 70° C. can be considered an appropriate benchmark (Vermeer et al. 2000. Biophysical Journal Volume 78:394-404 and Michnik et al. 2003. Journal of Thermal Analysis and Calorimetry 71:509-519). Data obtained using the IMER prepared as described below, provides empirical evidence of increased digestion efficiency at 70° C. in comparison to 60 and 50° ((FIGS. 6 and 8). Furthermore, according to the present invention the immobilized enzyme enables sustained operation at 70° C. (FIG. 11).

It is a protein's ability to maintain its tertiary structure that often dictates stability. For the purposes described above, it is desirable to obtain an enzyme that maintains its tertiary structure/specificity and activity under operating conditions in which the analyte of interest does not. The breakthrough in PCR came after the discovery of just such an enzyme, the Taq polymerase, found residing in the hot springs of Yellowstone Parks. Such thermally stable enzymes possess very interesting characteristics with a majority of hydrophobic amino acid residues residing on the inside of a protein's tertiary structure, protected from external aqueous environments; whereas the hydrophilic residues are found on the surface exposed to external aqueous environments (Korolev et al. 1995. Proceedings of the National Academy Of Sciences USA 92:9264-9268). Without wishing to be limited by theory, these enzymes have a hydrophobic core. Furthermore, charge is largely removed from the interior of the protein. Enzymes such as Taq polymerase have developed in such a way that changes in primary structure (the amino acid sequence) have led to the improved stability of the secondary and tertiary structure (the 3D structure). However, this is not always the case. The analysis of structure stability relationships shows that the structure of trypsin is not optimal with regard to the stability (Mozhaev et al. 1984. Enzyme and Microbial Technology 6:50-59). These "inefficiencies" enable certain functionalities (e.g. carrier protein binding) but also cause structural instability under non-physiological conditions. The discovery of a thermally stable, specific enzyme for broad application in proteomics is still pending. Stellwagen suggested the use of site-specific mutagenesis. However, these techniques are relatively complicated (Stellwagen 1984. Annals of the New York Academy of Sciences 434:1-6).

To reach the desired ends, polymerization of glycidol in BF3 can be used to obtain hydrophilic polymers with molecular weights ranging from 2500-6000 g/mol (Dworak et al. 1995. Macromolecular Chemistry and Physics 196: 1963-1970) Without wishing to be limited by theory, polymers of molecular weight 2500 g/mol are sufficient in size so as to preclude access to the interior of trypsin. Use of such polymers in the immobilization of trypsin induces hydrophilic modification at multiple sites on the exterior of the protein and therefore stabilizing the exterior of the protein while prohibiting the destabilization of the interior of the protein.

Following hydrophilization of external amino acids it is possible to further stabilize the trypsin via modification of the lysine residues using small hydrophobic modifiers. One such example is the use of N-hydroxysuccinimides. N-hydroxysuccinimides react with lysine residues forming hydrophobic esters. These reagents are small, which enables them to penetrate the interior of the enzyme. It is important that the treatment of an enzyme with N-hydroxysuccinimides be performed after hydrophilic modification of the proteins exterior, and that the hydrophilic modifier be sized so as to preclude any hydrophobic exterior modifications, otherwise both interior and exterior amino acids will be modified, destabilizing the three dimensional structure of the protein.

Following immobilization it was found that existing buffer compositions inadequately support the use of the immobilized enzyme at elevated temperatures. Serendipitously a discovery was made showing that very high concentrations of calcium chloride improved the activity/stability. Regarding the increase in activity/stability, using short run times and elevated temperature operating conditions it is difficult, if not impossible to differentiate between these two phenomena. Both a stable enzyme and buffer are necessary if the desired performance is to be obtained.

The immobilized enzyme can be configured to a variety of reactor formats. Ideally, the IMER format enables rapid uniform digestion and can be used in conjunction with both quantitative and qualitative analyses. As the operating temperature rises it becomes increasingly important that the reactor provide uniform heat conduction. Furthermore, a device or means of separating the immobilized enzyme from the reaction must be provided in order to obtain compatibility with downstream product analyses. It is also important that when necessary the reactor format provides a means of eliminating diffusion limitations.

Column Format

One form of the immobilized enzyme involves slurry packing into an open tubular/column system. The column can then be end-capped with liquid permeable frits. These frits provide a selective barrier, enabling the passage of sample solutions and precluding the passage of the immobilized enzyme. As such, samples and solutions can be pumped through the column by means of liquid chromatography (LC) pumping systems. The column housing itself should provide sufficient heat conduction. This column format is well suited for automation.

Multi-Well Formats

During sample preparation it is often desirable to process multiple samples at once, in parallel. Furthermore, such formats may be disposable such that the possibility of carry-over is eliminated. Such parallel processing enables significant time savings and can promote uniformity. In such cases an immobilized enzyme in the form of a multi-well or plate format is ideal. In such cases, uniform heat conduction across the multiple wells is important.

Reactor Materials

Typical materials used to make multi-well plates (e.g. polypropylene) exhibit poor heat transfer, making it difficult to uniformly process samples using an immobilized enzyme. In most experiments performed in protein analysis labs that utilized standard polypropylene plates, samples required 15 minutes to come to desired temperature and exhibited poor reproducibility. The delay in reaching uniform temperature and poor reproducibility of protein processing render the currently available IMERs not fit to high throughput protein analysis, especially for protein samples that are rare to obtain and/or difficult to produce. As such, to achieve fast and uniform processing it is important to engage the immobilized enzyme in a reaction vessel that is made from materials with rapid heat transfer capability; without limiting the scope of this concept, one example of such a reaction vessel is thin walled PCR type tubes or thin walled PCR or thin walled Eppendorf type plates. It is a requirement that good recovery from the materials used to make-up the reactor is obtained. Ideally the materials would be inert so as to induce increased recovery. In the absence of perfectly inert base materials, blocking reagents can be used to increase recovery. Examples of materials that would provide increase recovery in a variety of situations are bovine serum albumin, casein, fish gelatin, sugars, organic solvents, surfactants, chaotropes, detergents and salts.

Use of a Thermo Cycler

As discussed above, analytical reproducibility depends on the reproducible heating of the IMER during the sample preparation period. It is important that the heating apparatus is capable of providing uniform heating to all samples. One example as illustrated in this disclosure is a PCR thermo cycler. It is particularly well suited for this operation as its heated surface is usually made from a material that enables rapid heat transfer (such as silver), the heated sample interface extends a significant distance up the sides of the tube, and heat is provided from the top of the apparatus to eliminate condensation and further promote uniform results. While a thermo cycler has proven effective, it is possible that alternative heating apparatuses such as heating blocks, multi-channel heaters, water baths, ovens, microwave ovens or combinations thereof are also capable of providing the requisite uniform heating.

Use of a Combination Heater/Shaker

At any given time enzyme reactions are limited by either a lack of enzyme or diffusion limitations. In the column format, diffusion limitations can be minimized by pumping the mobile phase through materials containing very large pores. In these situations the stationary phase behaves similarly to a monolith. In the multi-well formats, diffusion limitations can be minimized through the use of agitation. In these cases sufficient mixing increases the reaction rate. An exemplary approach is to put the immobilized enzyme in a form of slurry into an apparatus that is undergoing vigorous shaking/heating. Alternatively, agitation in the form of rotation, end over end mixing, the use of a stir bar, sonicating (ultrasound), repeat pipetting or combinations thereof could be capable of providing the requisite agitation while a combination heater/shaker instrument, shaking in a convection oven, shaking in a water bath, and shaking in a microwave oven are example combinations capable of providing both heating and mixing.

Post-Reaction

After reaction with the immobilized enzyme, there are different ways of separating the immobilized enzyme from its reaction products for downstream analysis. Examples include but are not limited to using centrifugation or magnetic beads or other means commonly known in the art. For example, the sample/immobilized enzyme mix is transferred to a filter plate. A collection plate is placed beneath the filter plate and either positive pressure or vacuum is applied. The digested sample is then forced through the filter and collected into the collection plate. It is important that the filter frit size be liquid permeable but significantly smaller than the particle size of the immobilized enzyme stationary phase to prevent contamination of the sample with stationary phase. Ideally the liquid permeable barrier utilizes inert membranes for increased recovery. In the absence of perfectly inert materials, blocking reagents can be used to increase recovery. Examples of materials that would provide increase recovery in a variety of situations are bovine serum albumin, casein, fish gelatin, sugars, organic solvents, surfactants, sugars, chaotropes, detergents and salts.

Aggregation and Prevention

There are many situations in which the direct digestion of high concentrations of protein is advantageous. However, digestion of high concentrations of protein presents two primary hurdles. The first of these is the quantity of sample which must be acted upon by the trypsin to ensure complete digestion of the protein of interest. The second hurdle is the prevention of denaturation induced aggregation.

The rapid digestion of protein at high temperatures by the immobilized enzyme described herein overcomes the first of these hurdles. Simultaneously, however, the high temperatures which allow the first hurdle to be overcome induce aggregation of the thermally denatured proteins. This can be partially mitigated by rapid digestion itself, as peptide fragments are generally more soluble than large peptide chains. However, at the high concentrations of protein present in plasma or many other biologically derived samples, rapid digestion alone is insufficient to prevent aggregation. As such it is important to use additives for the prevention of aggregation. If a small loss in activity in the presence of such additives is observed, such an outcome is acceptable as long as sufficient digestion is obtained and elimination of aggregation is realized. Examples of such additives include but should not be limited to sugars, metals, detergents, surfactants, chaotropes, salts, organic solvents or combinations thereof.

Effect of Increased Calcium Chloride Concentration on Immobilized or Solution Based Enzyme Working System Trypsin as a protein contains lysines and arginines such that it may digest itself in a process called autolysis. Over the years different means of preventing or reducing autolysis have been developed. According to Nord et al. (1956. Archives of Biochemistry and Biophysics 66:120-131) $Ca^{2+}$ naturally present in most samples may bind at the $Ca^{2+}$ binding loop in trypsin and prevent autolysis. However, some literature purports that a $CaCl_2$ contribution is not absolutely necessary. These protocols recommend the use of ammonium bicarbonate (Wang et al., 2011. Proceedings of the National Academy of Sciences 108:2444-2449, and Thermo Scientific Pierce Protocol 89895, Promega Technical Manual #9PIV511), which is incompatible with $CaCl_2$ due to precipitation by means of calcium carbonate formation. Despite the controversies, a general consensus when using $CaCl_2$ is to only add about 1 mM of $CaCl_2$ in the digestion buffer. For example, Promega Technical Manual #9PIV511 and work by Sipos and Merkel (1970. An Effect of Calcium Ions on the Activity, Heat Stability, and Structure of Trypsin. Biochemistry 9:2766-2775), assert that calcium chloride used in concentrations above 1 mM has shown no additional benefit in improving enzyme stability. This disclosure departs from the established literature to explore higher concentrations of $CaCl_2$ in the reaction butter, and finds a surprisingly synergistic effect on enzyme efficiency when it is used in combination with the herein disclosed IMER. Other cations, such as $Na^+$, $Mg^{2+}$, $Ca^{2+}$, $Sr^{2+}$, $Mn^{2+}$, $Co^{2+}$, $Ni^{2+}$, $Zn^{2+}$, $Cu^{2+}$, $Fe^{3+}$ in various buffer solutions with high ionic strength may show positive enzyme reaction effect as well.

Magnetic Bead Format

It may also be the case where instead of immobilizing the enzyme on polystyrene alone, the enzyme is immobilized on a magnetized particle. In this case the material would reside in either a tube or plate format. During incubation the tube or plate can be loaded into a heater or combination heater/shaker apparatus. After incubation the plate assembly is brought into contact with a magnet so as to enable the separation of the immobilized enzyme from the analyte solution.

Enzymes

An exemplary immobilized proteolytic enzyme for use in digestion is trypsin. While the most popular proteolytic enzyme is trypsin, other enzymes with alternative functionalities may also be employed, such as chymotrypsin, Lys-C, Glu-C, Arg-C, Asp N, papain, pepsin, elastase, IdeS, pronase and PNGase F or combinations thereof, so that a variety of peptide products can be generated increasing the protein sequences that are observed and sequenced to provide more definitive identifications.

Stationary Phase Materials

An exemplary solid-support material for use in the digestion column is a polystyrene/divinylbenzene (PS/DVB) material. Other suitable solid-support materials may include other polystyrene-based materials, silica-based materials, controlled porosity glass and nitrocellulose-based materials, as well as materials containing a paramagnetic core for sample handling in robotic devices. The solid-support material may be in a particle form, or the solid-support material may be monolithic in form, a membrane, or planar in form. Also, microfluidic channels and the like may be advantageous.

Detectors

It is also within the scope of the present disclosure that the system may include a UV absorbance or fluorescence monitor for further analysis.

EXAMPLES

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person of ordinary skill in the art pertaining to this disclosure.

Example 1: Solution Digestion of Insulin Using a Typical Protocol

Figure 3:
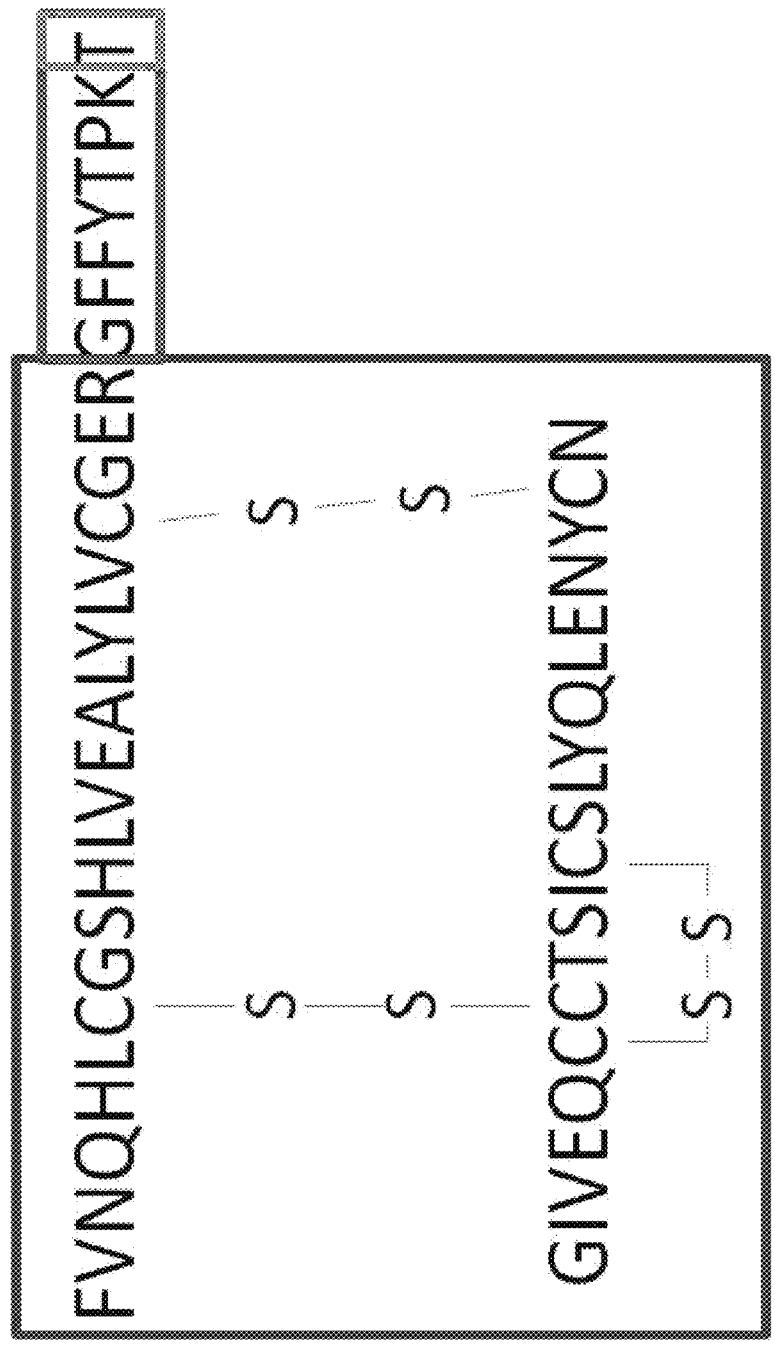
FIG. 3: Amino acid sequence of human insulin.

Insulin is often used as a model to demonstrate the importance of stoichiometric conversion of protein into signature peptides. When exposed to trypsin, human insulin forms two major products. There is a peptide with sequence GFFYTPK (SEQ ID NO 1) that resides near the C-terminus of protein, and there is the digested protein with sequence GIVEQCCTSICSLYQLENYCNFVNQHLCG-SHLVEALYLVCGER (SEQ ID NO 2). These two peaks are easily resolved from the intact protein with sequence GIVEQCCTSICSLYQLENYCNFVNQHLCG-SHLVEALYLVCGERGFFYTPKT (SEQ ID NO 3) using reversed phase chromatography. Visually, trypsin digestion of insulin generates three signature peptides as shown in FIG. 3: a large N-terminus peptide outlined in blue, a smaller C-terminus peptide outlined in red and a peptide consisting of a single amino acid alanine outlined in green.

In this example we monitored insulin digestion using a typical solution digestion protocol. Briefly, to a 100 ug/mL solution of insulin was added porcine trypsin to a final concentration of 2 ug/mL (50:1 protein:enzyme ratio). This sample was incubated at 37° C. for a total of 24 hours. At 30 minute, 1 hour, 3 hour, 6 hour, 12 hour, 18 hour and 24 hour time points 50 uL of this sample were removed. The resulting products were separated by reverse phase liquid chromatography and monitored by UV/Vis detection at 214 nm (FIG. 3). Mass spectral analysis indicated that the first peak in the chromatogram (Rt=4.5) corresponded to the peptide SEQ ID NO: 1 GFFYTPK. The second peak (Rt=5.6) corresponded to the protein product and the third peak (Rt=5.8) corresponded to undigested protein.

Figure 4A:
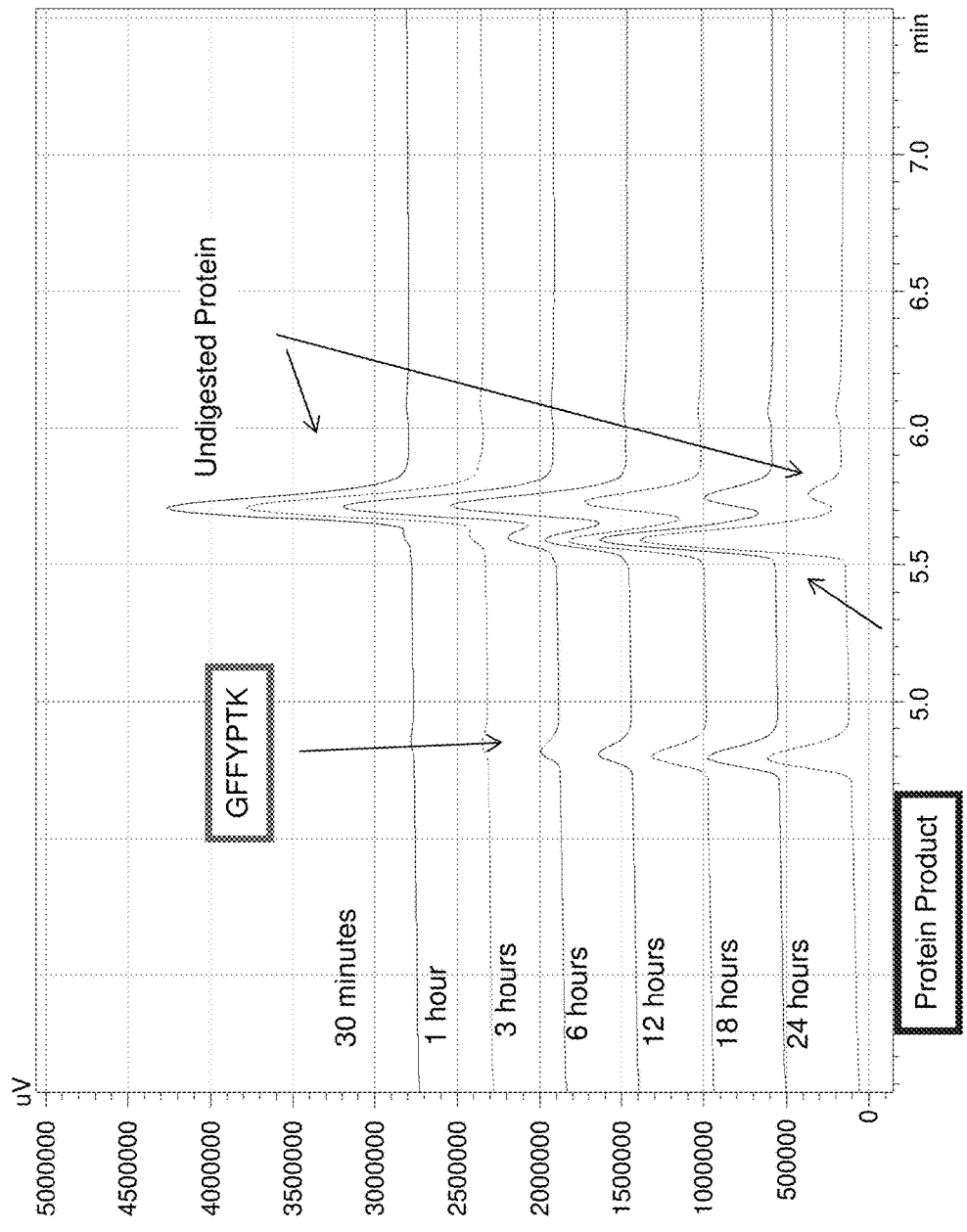
FIG. 4A: Chromatograms of insulin digested for various times using typical reaction conditions.
Figure 4B:
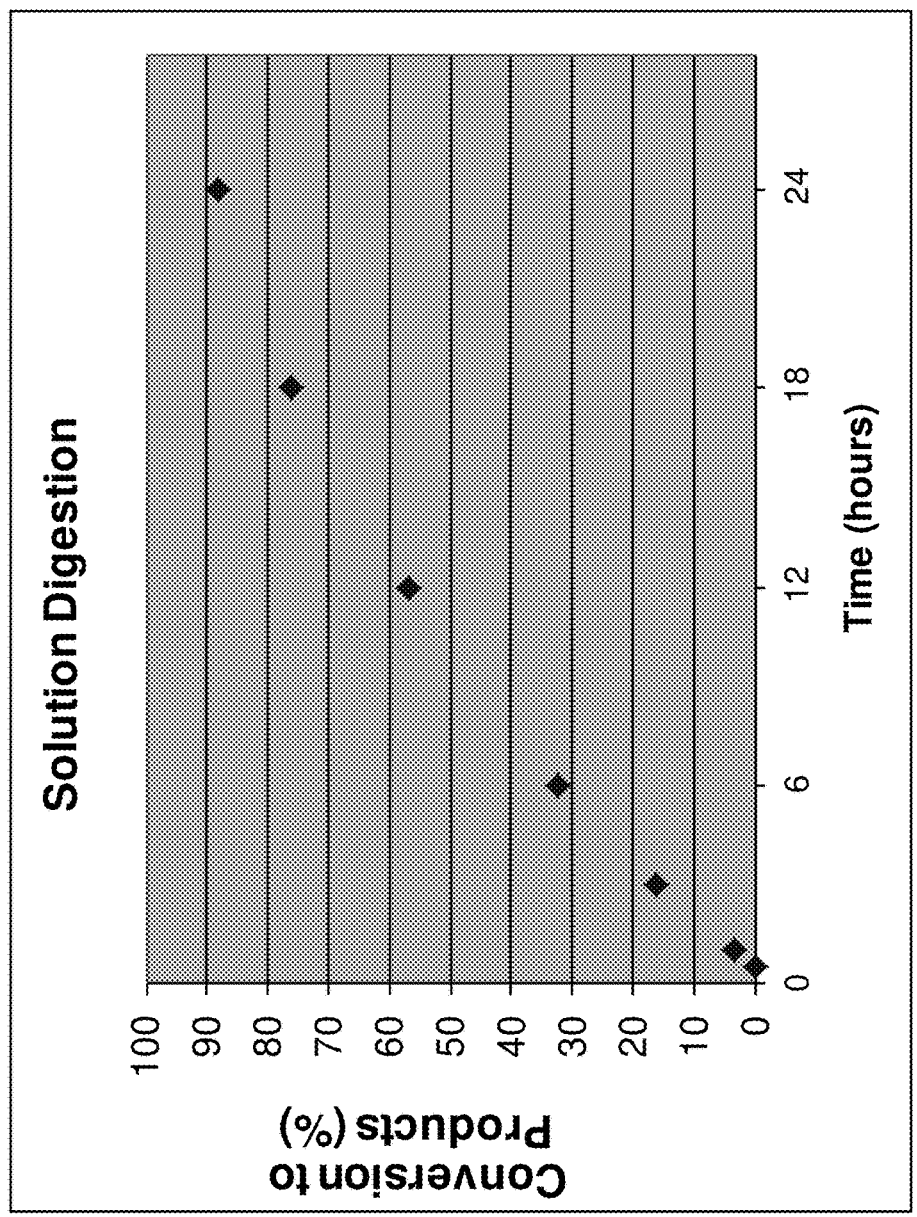
FIG. 4B: The conversion of insulin to products at various digestion times, using typical reaction conditions.

Monitoring the efficiency of this traditional approach to digestion (using a 50:1 protein:trypsin ratio, incubating at 37° C.) indicated that after 24 hours complete conversion to signature peptides had not been achieved (FIG. 4A).

Example 2: Making Improved Immobilized Enzyme

In a 50 mL reaction vessel were added 1.334 mL epibromohydrin, 0.666 mL glycidol, 15 mL dichloromethane and 50 uL boron trifluoride etherate. This reaction was allowed to incubate at room temperature for 24 hrs. After 24 hours the solvent was removed en vacuo. To this same reaction vessel 10 mL dH$_2$O, 7 mL polyethylene glycol, 30 mL IPA and 3 g PS-DVB were added. This flask was gently agitated for 14 hours. The resulting coated particle were filtered and collected in a clean round bottom flask. 10 mL 2 M KOH was added and the mixture gently agitated for 2 hours. After 2 hours 2 g sorbitol was added and the mixture gently agitated at room temperature for 12 hours. After 12 hours this mixture was filtered, washed with water and transferred to a clean round bottom flask. 100 mg sodium periodate was added to these materials and the resulting mixture incubated for 1 hour at room temperature. After 1 hour these materials were washed with 20 mL 50 mM sodium carbonate, filtered and collected into a large eppendorf.

150 mg of this material was added to a 15 mL eppendorf. To a separate eppendorf was added 1.2 g sodium sulfate diluted to 10 mL with water. 30 mg sodium cyanoborohydride was added to a separate 1.5 mL eppendorf and diluted with 1.5 mL 100 mM carbonate buffer, pH 9.6. 30 mg benzamidine was added to a separate 1.5 mL eppendorf and diluted with 1.5 mL 100 mM carbonate buffer, pH 9.6. 30 mg porcine trypsin was added to a separate 1.5 mL eppendorf and diluted with 600 uL of the benzamidine solution and transferred to the eppendorf containing the resin. To this resin containing eppendorf 720 uL of the sodium sulfate solution was added, 81 uL of the sodium cyanoborohydride solution was added and 840 uL of the 100 mM carbonate was added. This reaction mixture was gently agitated for 18 hours at room temperature. After 18 hours 200 mg benzamidine was added to a 15 mL eppendorf. The benzamidine was diluted in 10 mL carbonate buffer. The reaction mixture was centrifuged at 2000 rpm for 60 seconds, the solution was decanted, 2.5 milliliters of the fresh benzamidine solution added and the mixture vortexed. This wash cycle was repeated 2 more times so any unreacted, excess trypsin was removed. 30 mg sodium cyanoborohydride was added to a separate 1.5 mL eppendorf and diluted with 1.5 mL 100 mM carbonate buffer, pH 9.6. 81 uL of this solution was added and the reaction mixture gently agitated at room temperature for 4 hours. After 18 hours 200 mg benzamidine was added to a 15 milliliter eppendorf. 10 mL carbonate buffer was added to the benzamidine. The reaction mixture was centrifuged at 2000 rpm for 60 seconds, the solution decanted, 2.5 mL of the fresh benzamidine solution added and the mixture vortexed. This wash cycle was repeated 2 more times. 8 mg of acetic acid N-hydroxy succinimide was then added to the resin and the resulting reaction mixture incubated for 2 hours at room temperature. After 2 hours the resulting product was washed once with 100 mM carbonate buffer and 2 additional times with DMSO. 15 mg TPCK was added to a clean 1.5 mL eppendorf and dissolved in 200 mL DMSO. This solution was added to the resin and allowed to react for 2 hours. The resulting product was washed once with DMSO then 2 more times with tris-buffer saline pH 7.4.

Nitrogen analysis of these materials showed nitrogen content of 0.26%. This equates to a nitrogen content of 0.0026 g nitrogen/gram resin or 2.6 mg nitrogen/g resin or roughly 2.6 mg/mL. Using the Kjeldahl Method (2013. Critical Reviews in Analytical Chemistry 43:178-223) one can assume protein is roughly 16% nitrogen content. Therefore the 2.6 mg/mL is multiplied by 6.25 (equal to 100/16). As such one can consider the protein load of the final materials to have been approximately 16 mg trypsin/g resin.

Example 3: Immobilized Enzyme Column Synthesis 50 mg of material prepared as described in Example 2 was slurry packed into a 2.1×33 mm stainless steel column assembly.

Example 4: Automated System

Figure 7:
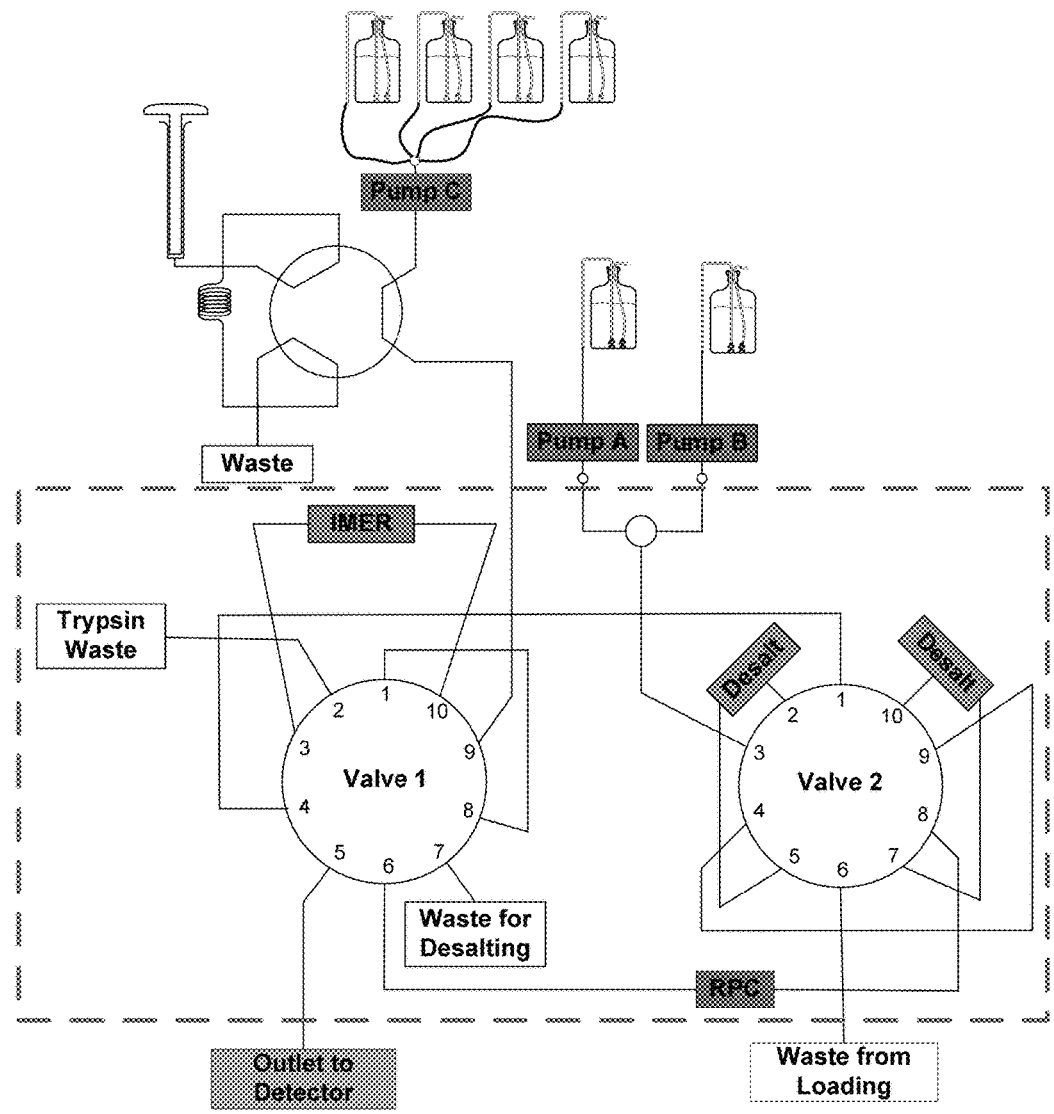
FIG. 7: Schematic of system used for the automation of enzyme digestion, desalting and reversed phase chromatography.
Figure 7A:
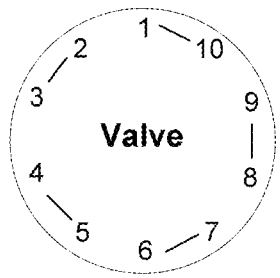
FIG 7A: position 1.
Figure 7B:
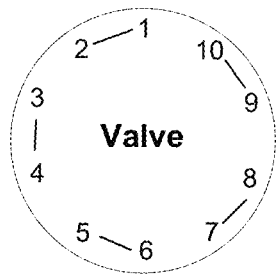
FIG 7B: position 2.

With reference to FIG. 7, an automated system was provided for protein digestion, recovery, and analysis. The system included an auto-sampler to initiate sample preparation. The system also included at least three columns coupled in series to the auto-sampler for further processing of the sample: (1) a digestion column, (2) a desalting column, and (3) a reverse phase chromatography (RPC) column. The columns could be maintained at an elevated temperature (e.g. 25-70° C.) in an oven compartment. The system further included a mass spectrometer coupled in series to the above-described columns. The auto-sampler could hold and house a plurality of sample vials. The auto-sampler could be refrigerated to minimize microbial growth in the sample vials. In addition to the plurality of sample vials, the auto-sampler could also hold and house any necessary solvents or reagents for reduction, alkylation, derivatization, proteolysis, internal standards addition, and dilution, for example, any of which can be aliquoted into sample vials in any order. A pump (Pump C) could have been provided to perform solvent selection, which could be a tertiary pump equipped with a solenoid valve. The system could be initiated by operating a robotic syringe to withdraw an aliquot of one or more desired solutions from the solution vials and to dispense the aliquot into a sample vial. Multiple solutions could be added sequentially to the sample vial, as might have been needed in reduction, alkylation, and proteolysis of a sample before analysis. After dispensing the solution into the sample vial, the syringe could be cleaned by taking in a suitable rinse solution and dispensing the rinse solution to waste. An exemplary rinse solution was 25% isopropyl alcohol in water. After a suitable incubation time in the sample vial, if any, the syringe withdrew an aliquot of the sample from the sample vial and loaded the aliquot onto a first valve (Valve 1), which was illustratively a 10-port valve having a first operative position (FIG. 7A) and a second operative position (FIG. 7B), where solid lines between ports indicate open flow paths. Valve 1 then directed the sample to the downstream digestion column (1). With Valve 1 in the second position (FIG. 7B), the sample illustratively entered Port 9, crossed over to Port 10, and then entered the digestion column (1). In the digestion column (1), protein in the sample underwent enzymatic digestion, which broke the protein apart into more easily identifiable peptide fragments. An exemplary digestion column (1) was an immobilized enzyme reactor (IMER), which included a proteolytic enzyme immobilized on a suitable solid-support material. The sample could be present in the digestion column (1) for about 1-5 minutes. The digestion column (1) could be about 33 mm in length, for example. The digested sample from the digestion column (1) returned to Valve 1. With Valve 1 in the second position (FIG. 7B), the digested sample from the digestion column (1) entered Port 3, crossed over to Port 4, and then continued to Port 1 of a second valve (Valve 2). Alternatively, with Valve 1 in the first position (FIG. 7A), the material from the digestion column (1) would enter Port 3, cross over to Port 2, and then continue to waste, such as to rinse the digestion column (1). Like Valve 1, Valve 2 was also illustratively a 10-port valve having a first operative position (FIG. 7A) and a second operative position (FIG. 7B). Valve 2 was illustratively coupled to two desalting columns (FIG. 7). In each desalting column (2), the peptide fragments from the digestion column (1) adhered to a hydrophobic surface. Exemplary hydrophobic surfaces were polystyrene divinyl benzene (PS-DVB) and octadecyl silane (C18). Salt ions that were present along with the peptide fragments did not adhere to the desalting column (2) and were washed away to waste. For example, with Valve 2 in the first position (FIG. 7A), the digested sample from the digestion column (1) illustratively entered Port 1, crossed over to Port 10, and then entered the desalting column (2b). Salt ions that did not adhere to the desalting column (2b) illustratively returned to Valve 2 via Port 7, crossed over to Port 6, and were diverted to waste. After desalting, the adhered peptide fragments were washed away from the desalting column (2) using a suitable solvent that was delivered from Pump A and/or Pump B. The solvent make-up is described further below. With Valve 2 now turned to the second position (FIG. 7B), the solvent illustratively entered Port 3, crossed over to Port 4, traveled to Port 9, crossed over to Port 10, and then entered the desalting column (2b). Together, the once-adhered peptide fragments and the solvent from the desalting column (2) entered Port 7, crossed over to Port 8, and then continued to the RPC column (3). In the RPC column (3), the peptide fragments were gradient-separated based on their hydrophobic/hydrophilic interactions. The RPC column (3) could include a hydrophobic or non-polar stationary phase, such as octadecyl silane (C18). The above-described solvent from Pump A and/or Pump B could serve as a gradient mobile phase. An exemplary solvent was formed by combining a first solution of 2% acetonitrile, 98% water and 0.1% formic acid from Pump A with a second solution of 90% acetonitrile, 10% water and 0.1% formic acid from Pump B. The gradient could be achieved over time by increasing the concentration of one solution (e.g., the second solution from Pump B) and decreasing the concentration of the other solution (e.g., the first solution from Pump A). More hydrophilic or polar materials would elute from the RPC column (3) first, while more hydrophobic or non-polar materials would be retained within the RPC column (3).

The peptide fragments from the RPC column (3) could then be directed to a mass spectrometer for peptide sequence analysis. The peptide sequence could be compared with predicted sequences correlated to genomic databases and find matching signature sequences that could be used to identify the protein parent from which the peptide sequence was derived, for example. With Valve 1 in the second position (FIG. 7B), the material from the RPC column (3) illustratively entered Port 6, crossed over to Port 5, and continued to the mass spectrometer. Alternatively, with Valve 1 in the first position (FIG. 7A), the material from the RPC column (3) illustratively entered Port 6, crossed over to Port 7, and was then diverted to waste. While the column system was well suited for use in an automated format, samples had to be processed one at a time, serially.

Example 5: Digestion of Insulin Using an Immobilized Enzyme Prepared as Described Above Digestion of insulin using an immobilized enzyme prepared as described in Example 2 in a column format prepared as described in Example 3 was determined at various temperatures following the parameters set in Table 1. These experiments were performed using an automated system as described in Example 4

TABLE 1

Human insulin digestion and analysis using immobilized
enzyme column prepared according as described above.

| | |
|---|---|
| Sample | 100 ug/mL Hu Insulin |
| Injection Volume | 50 uL |
| Digest Conditions | Time-Varies, Temperature - 70° C. |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes |
| UV/Vis | 214 |

Figure 5:
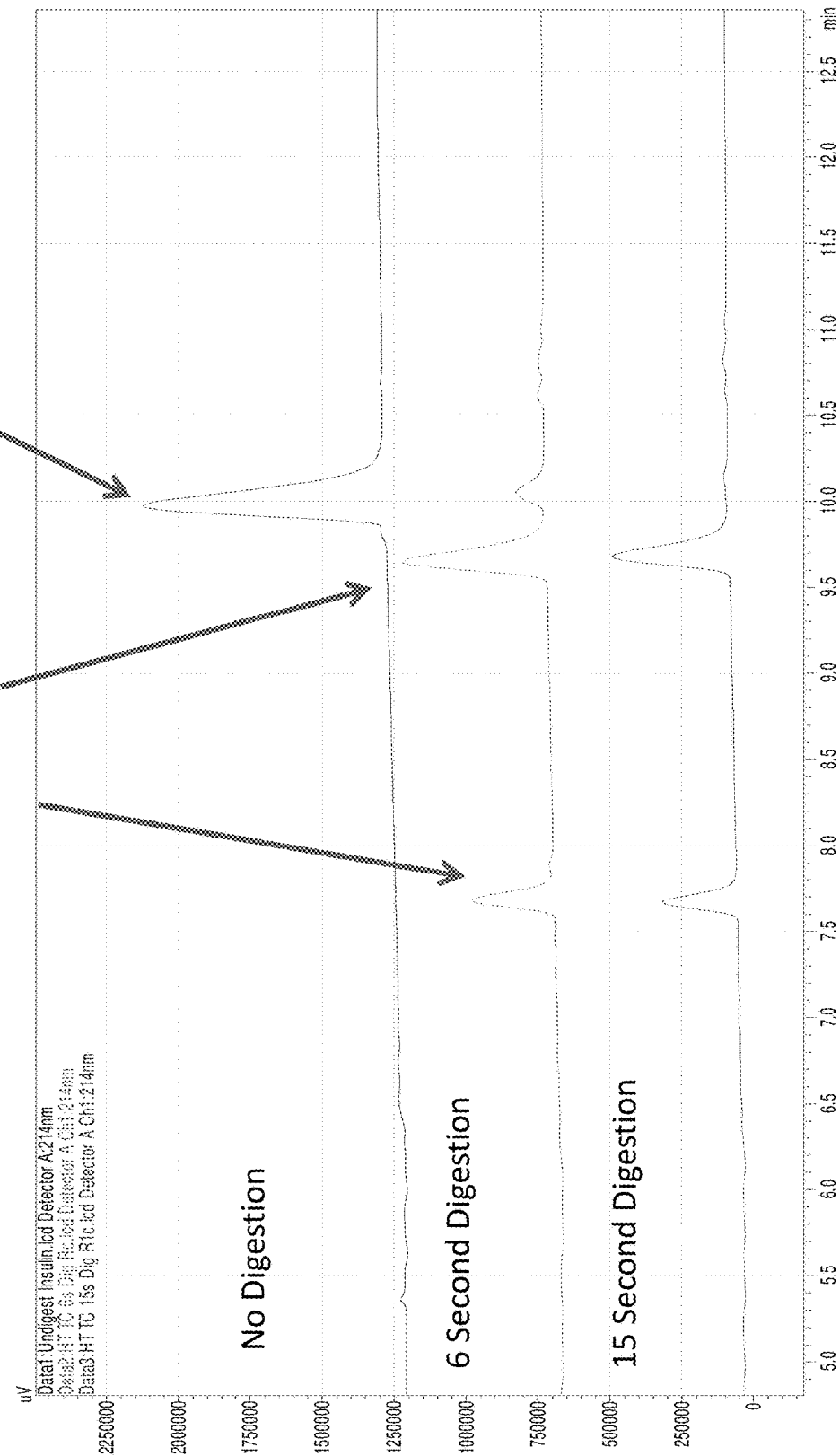
FIG. 5: Digestion of insulin using the immobilized enzyme prepared according to Example 2, packed in a column prepared according to Example 3 and processed using the automated system described in Example 4.

Briefly, the trypsin column was brought up to 70° C. in the column oven. 50 mL aliquots of a 100 mg/mL solution of insulin were injected into the 2.1×33 mm trypsin column prepared according to the description herein. The protein sample was digested using a flow-through format with the residence time in the column being controlled as a function of the flow rate of the mobile phase. A set of 2 insulin samples were digested for 6 and 15 seconds as shown by the middle and bottom chromatograms respectively. The resulting products were separated by reverse phase liquid chromatography and monitored by UV/Vis detection at 214 nm. The first peak in the chromatogram (Rt=7.7) corresponded to the peptide SEQ ID NO: 1 GFFYTPK. The second peak (Rt=9.7) corresponded to the protein product and the third peak (Rt=10.1) corresponded to undigested protein. A control experiment, performed with no trypsin column in place (top chromatogram) showing undigested insulin. A complete insulin digestion was achieved in as short a time as 15 seconds (FIG. 5, bottom graph).

It is of significance that an immobilized enzyme reactor reduced digestion time to seconds. This provides ample time for a manufacturing process to respond to any protein structure errors or to take any further action based on the fast profiling of the target protein. For decades the industry has been trying to achieve quick and complete protein profile analysis, and this study has supplied a viable strategy to solve the problem. It is also important to note the absence of additional peaks, especially those associated with specific trypsin digestion. In the presence of autolysis or post-translational modification additional peaks are observed by UV-Vis. The absence of such peaks validates the maintained specificity of the immobilized enzyme at these operation temperatures.

Figure 9:
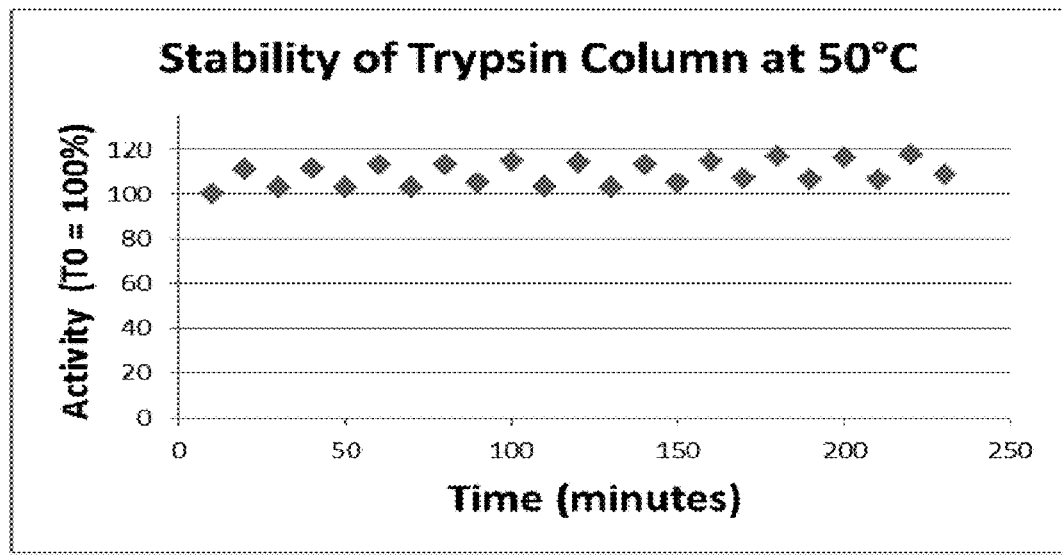
FIG. 9: Data showing sustained activity at 50° C. Immobilized enzyme prepared according to Example 2, packed in a column prepared according to Example 3 and samples processed using the automated system described in Example 4.
Figure 10:
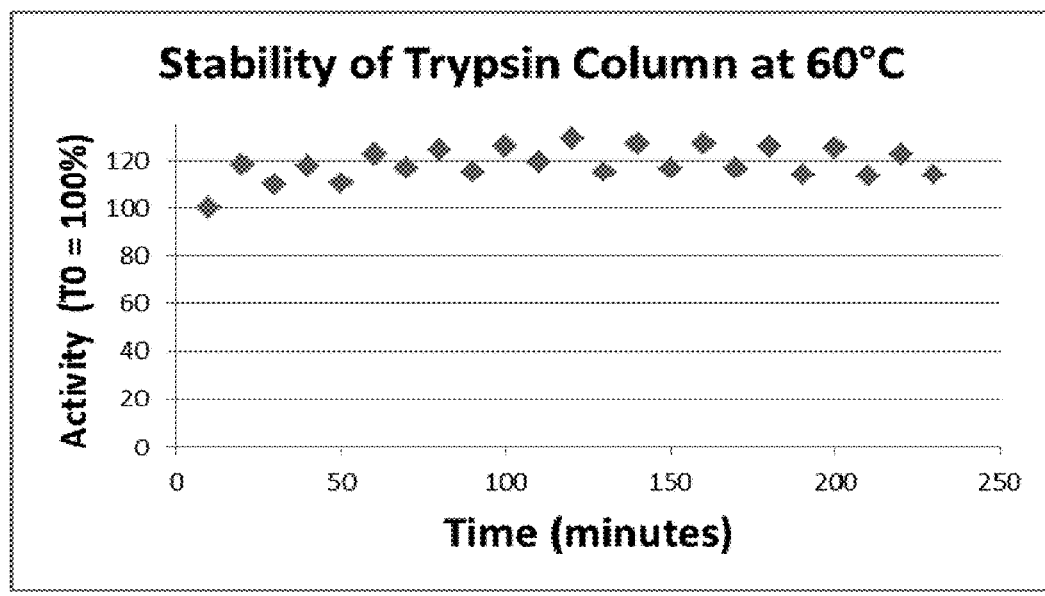
FIG. 10: Data showing sustained activity at 60'C. Immobilized enzyme prepared according to Example 2, packed in a column prepared according to Example 3 and samples processed using the automated system described in Example 4.

Example 6: Immobilized Enzyme Temperature Stability Determinations Using Human Insulin as Substrate Temperature stability of an immobilized enzyme prepared as described in Example 2 in a column format prepared as described in Example 3 was determined at various temperatures following the parameters set in Table 2. These experiments were performed using an automated system as described in Example 4. All columns demonstrated stability at all temperatures tested (50-70° C.). See (FIGS. 9-11). The peak area generated by the mass spectrometer at time point 0 was designated 100% activity such that activity measurements were compared to this initial measurement and activity reported as a percent.

It is a surprising result to anyone in the art that, as FIGS. 9-11 indicate, the enzyme activity is comparable to its initial activity even after 2 hours of exposure at 50° C., 60° C. or 70° C. Higher temperatures were not assessable due to the limitations of this instrument's heating element, but it is possible that the temperature stability of these materials exceeds 70° C. given that no significant temperature derivational trend was observed over the course of these studies. It is proven that according to the Perfinity protocol described above, enzymes immobilized and modified are able to withstand higher denaturing condition temperatures with sustained activity. Therefore, the IMER produced in this study provides an unexpected result in the enzyme immobilization practice.

TABLE 2

Parameters used for the evaluation of immobilized enzyme stability

| | |
|---|---|
| Sample | 1 ug/mL Hu Insulin |
| Injection Volume | 2 uL |
| Digest Conditions | 1 minute, Temperature - Varies |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes |
| MS1/MS2 | SEQ ID NO: 1 GFFYTPK - 430.2/655.2 |

Example 7: Destabilization by Means of Hydrophilization

An immobilized enzyme was made increasingly hydrophilic by means of nitrosylation using the nitration and amination protocols described by Mozheav (1988. European Journal of Biochemistry 173:147-154).

Temperature stability testing was performed in a column format prepared as described in Example 3. These experiments were performed using an automated system as described in Example 4. This column showed decreased stability in comparison to immobilized enzyme prepared according to Example 3. Parameters used for this evaluation are summarized in Table 3 below.

TABLE 3

Parameters used for the evaluation of immobilized enzyme stability

| | |
|---|---|
| Sample | 1 ug/mL Hu Insulin |
| Injection Volume | 2 uL |
| Digest Conditions | 1 minute, Temperature 70° C. |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes |
| MS1/MS2 | SEQ ID NO: 1 GFFYTPK - 430.2/655.2 |

Results are summarized in Table 4 below.

TABLE 4

Determination of immobilized enzyme
stability following hydrophilization

| Time at 70° C. (min) | Activity Lost (%) from T = 0 |
|---|---|
| 15 | 0 |
| 30 | 16 |
| 45 | 15 |
| 60 | 10 |
| 75 | 11 |
| 90 | 13 |
| 105 | 16 |
| 120 | 17 |
| 135 | 17 |
| 150 | 18 |
| 165 | 20 |
| 180 | 20 |

TABLE 4-continued

Determination of immobilized enzyme stability following hydrophilization

| Time at 70° C. (min) | Activity Lost (%) from T = 0 |
|---|---|
| 195 | 22 |
| 210 | 24 |
| 225 | 29 |
| 240 | 28 |
| 255 | 29 |
| 270 | 30 |
| 285 | 31 |
| 300 | 34 |

Example 8: Demonstration of Improved Immobilized Enzyme Reactor Preserving Optimum Enzyme Thermal Stability and Activity at Elevated Temperature Using Human IgG as Substrate As previously described, column stability at 60° C. and 70° C. is very important for the analysis of biomolecules, namely immunoglobulin Gs. As described above, there is a precedent for the denaturation of the variable region of an antibody at 60° C. and its constant region at 70° C. (Vermeer et al. 2000. Biophysical Journal 78:394-404). It is frequently desirable to perform digestion of IgG constant regions at higher temperature so that a complete sequence analysis is possible. Ideally such a sequence analysis could be performed rapidly so as to enable monitoring of the quality of IgGs during synthesis and production. If any deviation of quality is observed during production the reaction can quickly be quenched or the reaction conditions altered so that the production batch might be preserved. Using standard conditions monitoring can be performed only following overnight digestion which prohibits rapid decision making (delayed reaction monitoring). Temperature stability of an immobilized enzyme prepared as described in Example 2 in a column format prepared as described in Example 3 was determined at various temperatures following the parameters set in Table 5. These experiments were performed using an automated system as described in Example 4. Testing at various temperatures confirmed digestion at 70° C. as well as the importance of running at this temperature as opposes to lower temperatures. These results also indicated that the materials described here-in have solved the problems associated with delayed reaction monitoring.

Briefly, native IgG was subjected to a variety of temperatures and digested using a variety of digestion times. The effectiveness of digestion was then determined by monitoring signature peptide VVSVLTVLHQDWLNGK (SEQ ID No: 4). Furlong et. al. established the importance of this peptide. (2012, *Biomedical Chromatography* 26:1024-1032). This peptide is unique and specific to human monoclonal IgGs. A large number of bio therapeutics are humanized monoclonal antibodies. As such, the monitoring of this peptide is used as part of a variety of drug development stages.

Using this peptide as an indicator, following the parameters set forth in Table 5 below, it was shown IgG has poor digestion at low temperature operating conditions (50-60° C.). However, using Perfinity's new immobilized enzyme column formulation described in this work, IgG is effectively digested at 70° C. See FIG. 6. This shows that the Perfinity's formulated IMER can effectively be used to analyze monoclonal antibodies, especially those digestions that need to be performed in harsh temperature denaturing conditions.

TABLE 5

Parameters used for the evaluation of native IgG digestion at various temperatures

| | |
|---|---|
| Sample | 1 ug/mL Hu IgG |
| Injection Volume | 2 uL |
| Digest Conditions | 50-70° C., 30-120 seconds; Varies according to chart |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes |
| MS1/MS2 | (SEQ ID NO: 4) VVSVLTVLHQDWLNGK-603.67/805.62 |

Example 9: Investigation of Improved Immobilized Enzyme in Standard Polypropylene Plate 15 uL of the immobilized enzyme prepared according to Example 2 was pipetted into each well of a deep-well polypropylene plate.

TABLE 6

Shows a poor reproducibility of immobilized enzyme in standard 96-well Plate

Reaction Conditions

| | |
|---|---|
| Equipment | Convection Oven Equipped with 96 Well Plate Shaker |
| Sample | 200 uL Hu IgG$_1$ (varying concentration) |
| Digest Temperature Setting | 72.5° C. |
| Time | 90 minutes |
| Resin Amount | 15 uL |

LCMS Conditions Used for Analysis of Recovery

| | |
|---|---|
| Injection Volume | 10 uL |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | VVSVLTVLHQDWLNGK (SEQ. ID. NO. 4) - 937.94/836.39 |

| | Analyte Concentration (ng/mL) | | | | |
|---|---|---|---|---|---|
| | 123 | 370 | 1111 | 3333 | 10000 |
| Row 1 | 860 | 2338 | 6084 | 26162 | 103124 |
| Row 2 | 1528 | 1921 | 6459 | 43738 | 142165 |
| Row 3 | 1123 | 3353 | 7596 | 35235 | 174348 |
| Row 4 | 812 | 2886 | 6242 | 14166 | 70910 |
| Average | 1081 | 2625 | 6595 | 29825 | 122637 |
| StDev | 328 | 626 | 685 | 12668 | 45136 |
| CV(%) | 30 | 24 | 10 | 42 | 37 |

It was clear that the use of the immobilized enzyme in this standard format resulted in unacceptably high variation.

Example 10: Determination of Time Required to Bring Samples to Temperature in Standard Polypropylene Plate In a follow-up study a sample was placed near the center of the 96 well plate. An Immersion Temperature Probe connected to a FLUKE 51 II Digital Thermometer was immersed in the sample. The convection oven was set to 72.5° C. It took approximately 10 minutes for the sample to reach a temperature of 65° C. and approximately 15 minutes for the sample to reach a temperature of 70° C. This demonstrated a need for other materials to obtain a rapid and consistent digestion.

Example 11: Immobilized Enzyme PCR Strip of 8 Format 15 uL of the immobilized enzyme prepared according to Example 2 was pipetted into each well of a PCR strip of 8.

Example 12: Sample Processing by Filtration

Samples were added to the immobilized enzyme reactor prepared according to Example 9, transferred to a sample heater or alternatively a device that provides both heating and agitation, incubated, then the samples transferred to a filter plate. The filter plate was placed on top of a collection plate then either vacuum or positive pressure was applied forcing the liquid solutions through the filter and into the collection plate.

Example 13: Sample Processing by Centrifugation

In one embodiment samples were added to the immobilized enzyme reactor prepared according to Example 9, transferred to a sample heater or alternatively a device that provides both heating and agitation, incubated, then the samples were transferred to a centrifuge. After centrifugation the liquid solutions were decanted and transferred to a separate plate or vial.

Example 14: Results of Using PCR Plate as the Reaction Vessel

An improved IMER was created by adding 15 uL of slurry prepared as previously described to the bottom of a 200 uL, strip of 8 PCR tubes prepared as described in Example 9. Samples were added directly to this slurry without pretreatment (neither reduction nor alkylation were required). Samples were heated using a ThermoMixer equipped with a PCR adapter. 12 strips of 8 could be processed simultaneously. Following incubation the entire sample was removed using a multichannel pipette and transferred to a filter plate. A collection plate was placed below the filter plate and positive pressure was applied separating the immobilized enzyme from the digested sample.

Example 15: Evaluation of Relevant Reactor Materials

Buffer A=127 g Tris HCl, 68 g Tris Base, 8.77 g NaCl, 1.1 g $CaCl_2$, 20 mL IPA are added to a large reservoir and the total volume of the solution brought to 1 L.

Human, monoclonal IgG1 was used in this experiment. In this work, Perfinity formulated immobilized enzyme reactor was used to create a calibration curve of IgG1 without going through an alkylation and reduction process. In each of 5 wells of a PCR tube 15 uL of slurry prepared as described above was added to an eppendorf tube. 5, 200 microliter samples of IgG1 at concentrations ranging from 123 ng/mL-10,000 ng/mL (10,000 ng/mL, 3,333 ng/mL, 1,111 ng/mL, 370 ng/mL, and 123 ng/mL) were made via serial dilution in Buffer A with 0.1% casein. Casein is a protein that is frequently used to eliminate non-specific binding by blocking active sites 200 microliters of each of these samples was added to the wall of a PCR tube. These 5 samples were placed in a ThermoMixer set to a temperature of 85° C. and shaken at 1400 RPM for 60 minutes. The samples were removed from the ThermoMixer, filtered, washed and the digest materials transferred to the autosampler of a LC/MS. These samples were analyzed according to the parameters set forth in Table 7 below.

TABLE 7

Determination of the recovery of peptides from PCR thermo cycler used in combination with an immobilized enzyme

| Reaction Conditions | |
|---|---|
| Equipment | ThermoMixer Equipped with a PCR Adapter |
| Sample | 200 uL Hu $IgG_1$ (varying concentration) |
| Digest Settings | 80° C., 1400 RPM |
| Time | 1 hour |
| Digest Buffer | Buffer A, 0.1% casein |
| Wash Buffer | Buffer A, 0.1% casein |
| WB Volume | 200 uL |
| Resin Amount | 15 uL |
| LCMS Conditions | |
| Injection Volume | 5 uL |
| Sample | Hu $IgG_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK (SEQ ID NO: 5) - 937.74/836.43 |
| Results | |

| Analyte (IgG1) Concentration (ng/mL) | Analyte Response (Area Counts) |
|---|---|
| 123 | 860 |
| 370 | 2338 |
| 1111 | 6024 |
| 3333 | 26114 |
| 10000 | 103695 |

Figure 12:
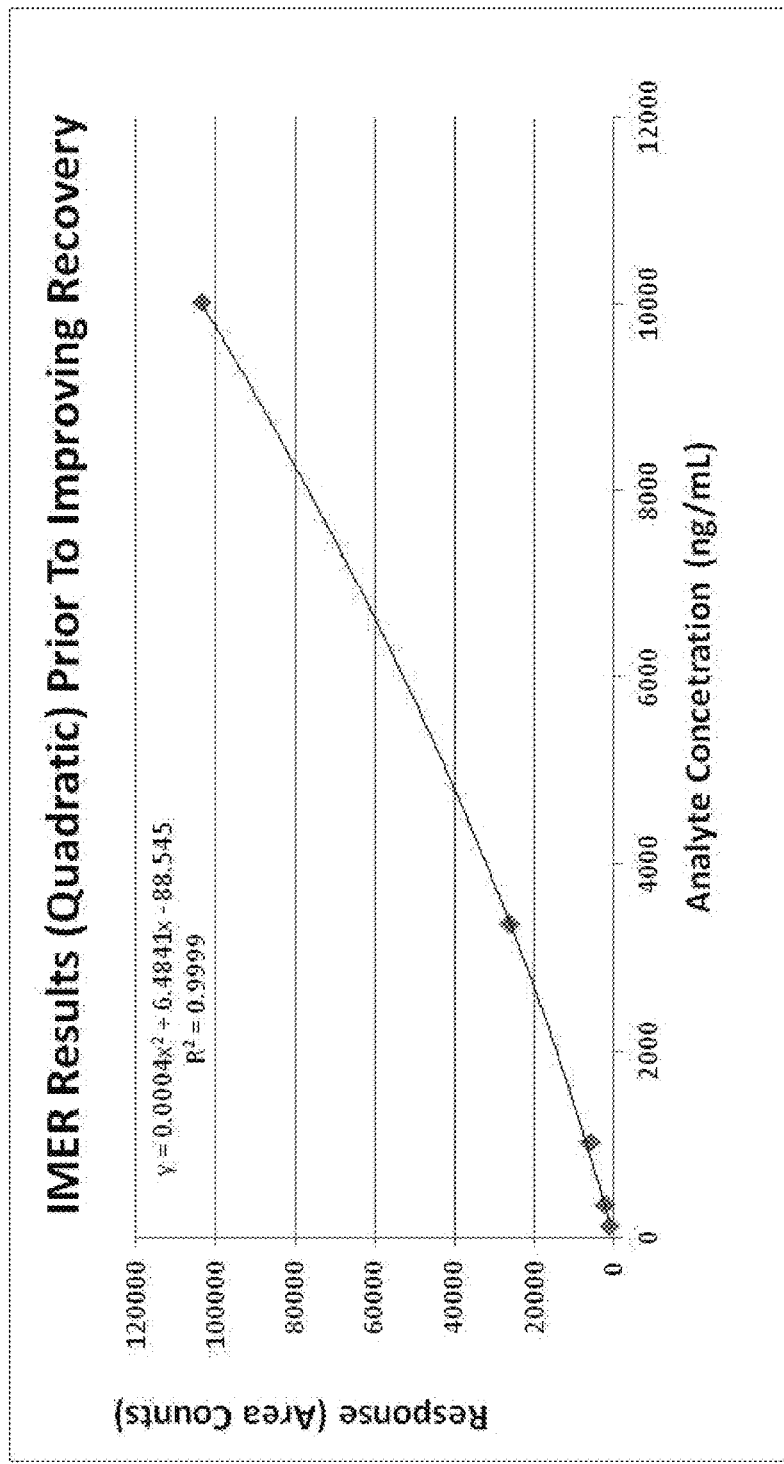
FIG. 12: Results Prior to Improving System Recovery. Immobilized enzyme prepared according to Example 2, packed in a strip of 8 format prepared according to Example 9 and samples processed according to Example 11. The quadratic curve formed when plotting the results indicated there was a lack of recovery.

Although the multi-well reaction format provides efficient digestion and simultaneous processing of samples, the quadratic curve FIG. 12 formed when plotting the results indicated there was a lack of recovery from the plate materials used.

Example 16: Improving Recovery from the System

In this example we show the procedure of identifying possible retention using the IMER provided in Table 11. It is worth noting that the materials used for the filter plate play a role in the recovery, typically use of inert or hydrophilic materials for the filter plate frit is more effective for the increased recovery.

In order to determine the source of retention a set of experiments was performed where a sample of predigested solution (typically 1 mL in volume) was added to a collection plate (Sample 0). Half of this sample (typically 500 uL) would then be added to the material in question (e.g. digestion vessel, resin, filter plate, collection plate) and agitated. The sample exposed to the material in question would then be transferred to yet another well of material in question. This process would be repeated until the predigested sample had been exposed to 5 wells of the material in question. This sample would then be transferred to a collection plate for analysis (Sample 6). This procedure exacerbates any retention to materials making it clear to see where losses in recovery are occurring.

In order to isolate the digestion products the sample and IMER materials are transferred to a filter plate with a 0.4 um pore size frit filter. This frit filter can be made of a variety of materials including but not limited to polypropylene, glass, GHP (hydrophilic polypropylene) or Polytetrafluoroethylene (PTFE). A collection plate is placed below the filter plate and positive pressure is applied to the top of both the stack. The pressure forces the solution through the frit filter while the particles remain above the filter. Give the large surface area of the frit filter, the materials use can significantly impact recovery. As such, recovery from the filter plate was tested using the recovery testing procedure described above. The results from these experiments can be seen in Table 8 below.

TABLE 8

Testing of recovery from various materials in presence of blocker casein

Reaction Conditions for Generating Starting Materials

| Equipment | ThermoMixer Equipped with a PCR Adapter |
|---|---|
| Sample | 200 uL Hu IgG$_1$ (varying concentration) |
| Digest Settings | 80° C., 1400 RPM |
| Time | 1 hour |
| Digest Buffer | Buffer A |
| Wash Buffer | Buffer A |
| WB Volume | 200 uL |
| Resin Amount | 15 uL |

LCMS Conditions Used for Analysis of Recovery

| Injection Volume | 5 uL |
|---|---|
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK (SEQ ID NO: 5) - 937.74/836.43 |

| Material Tested/ Sample Number | Analyte Response (Area Counts) | Percent Loss |
|---|---|---|
| Polypropylene Filter Plate Sample 0 | 6834 | N/A |
| Polypropylene Filter Plate Sample 6 | 9037 | −32.24 |
| GHP Filter Plate Sample 0 | 6896 | N/A |
| GHP Filter Plate Sample 6 | 7557 | −9.59 |

The increase in signal suggests that casein in the sample was causing suppression of the mass spectrometry signal and that this suppressant was being removed during filtration.

Given the recovery issues demonstrated in Example 13, each individual component of the IMER system was tested for recovery. In general, PCR tubes, pipette tips and collection plates are made of polypropylene. As such it was important to determine the extent to which protein samples adhered to polypropylene.

In order to determine the retention to polypropylene a sample of 10 ug/mL IgG was digested offline. 900 uL buffer was added to the material to be tested followed by a 100 uL addition of predigested IgG1 (Sample 0). Half of this sample was then added to another well of the material in question. The sample exposed to the material in question would then be transferred to yet another well of material in question. This process was repeated until the predigested sample had been exposed to 5 wells of the material in question. This sample was transferred to a collection plate for analysis (Sample 6). In this experiment standard polypropylene (PP) was compared to Eppendorf LoBind™.

TABLE 9

Testing of recovery from sample vials made of various materials

Reaction Conditions for Generating Starting Materials

| Equipment | Thermo Mixer Equipped with a PCR Adapter |
|---|---|
| Sample | 200 uL Hu IgG$_1$ (varying concentration) |
| Digest Settings | 80° C., 1400 RPM |
| Time | 1 hour |
| Digest Buffer | Buffer A |
| Wash Buffer | Buffer A |
| WB Volume | 200 uL |
| Resin Amount | 15 uL |

LCMS Conditions Used for Analysis of Recovery

| Injection Volume | 10 uL |
|---|---|
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK (SEQ. ID. NO. 5) - 937.74/836.43 |

| | Analyte Response (Area Counts) | Percent Loss |
|---|---|---|
| PP Vials sample in Buffer A Sample 0 | 20836 | N/A |
| PP Vials sample in Buffer A Sample 6 | 10736 | 48 |
| LoBind Vials sample in Buffer A Sample 0 | 19743 | N/A |
| LoBind Vials sample in Buffer A Sample 6 | 18266 | 7 |

These results show that significant amounts of analyte were adhering to polypropylene while lesser amounts of material were adhering to LoBind.

Polypropylene is a very common material in the laboratory. Furthermore, for this IMER format it is extremely important to obtain robust/uniform heating. This is readily achieved through the use of thin walled PCR plates and tubes. Unfortunately these materials are not available in LoBind formats. As such an alternative means of increasing recovery was required. The use of casein as a blocking agent was deemed nonviable since it can suppress MS signal. A follow-up experiment showed that BSA at levels at or above 0.05% could be used to enhance recovery. As shown in Table 10, this additive enabled the use of thin walled PCR tubes with uniform heating and high recovery.

TABLE 10

Testing of the influence of buffer on recovery

Reaction Conditions for Generating Starting Materials

| Equipment | ThermoMixer Equipped with a PCR Adapter |
|---|---|
| Sample | 200 uL Hu IgG$_1$ (varying concentration) |
| Digest Settings | 80° C., 1400 RPM |
| Time | 1 hour |
| Digest Buffer | Buffer A, BSA (varying concentration) |
| Wash Buffer | Buffer A, BSA (varying concentration) |
| WB Volume | 200uL |
| Resin Amount | 15 uL |

TABLE 10-continued

Testing of the influence of buffer on recovery

LCMS Conditions Used for Analysis of Recovery

| | |
|---|---|
| Injection Volume | 2 uL |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK (SEQ. ID. NO. 5) - 937.74/836.43 |

| | Analyte Response (Area Counts) | Percent Loss (%) |
|---|---|---|
| PP Vials sample in Buffer A 0.01% BSA Sample 0 | 3564 | N/A |
| PP Vials sample in Buffer A 0.01% BSA Sample 6 | 2945 | 17 |
| PP Vials sample in Buffer A 0.05% BSA Sample 0 | 3460 | N/A |
| PP Vials sample in Buffer A 0.05% BSA Sample 6 | 3418 | 1 |

Next, the impact of the resin on the percent recovery was investigated (Table 11). These results showed while materials were lost upon exposure to the filter apparatus, no additional materials were absorbed by the resin itself. This data shows that the resin itself is not retaining significant amount of analyte, a highly advantageous feature.

TABLE 11

Testing of the influence of the immobilized trypsin resin on recovery

Reaction Conditions for Generating Starting Materials

| | |
|---|---|
| Equipment | ThermoMixer Equipped with a PCR Adapter |
| Sample | 200 uL Hu IgG$_1$ (varying concentration) |
| Digest Settings | 80° C., 1400 RPM |
| Time | 1 hour |
| Digest Buffer | Buffer A |
| Wash Buffer | Buffr A |
| WB Volume | 200 uL |
| Resin Amount | 15 uL |

LCMS Conditions Used for Analysis of Recovery

| | |
|---|---|
| Injection Volume | 5 uL |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK(SEQ. ID. NO. 5) - 937.74/836.43 |

| | Analyte Response (Area Counts) | Percent Loss (%) |
|---|---|---|
| GHP filterplate into LoBind Collection Plate Sample 0 | 18266 | N/A |
| GHP filterplate into LoBind Collection Plate Sample 6 | 14888 | 18 |
| GHP filterplate into LoBind Collection Plate with 15 uL Resin Sample 0 | 20226 | N/A |
| GHP filterplate into LoBind Collection Plate with 15 uL Resin Sample 6 | 16733 | 17 |

In order to minimize sample loss during filtration, BSA was added to Buffer A for this step of the process. This reduced the sample loss to less than 2% per well (9% after exposure to 5 wells).

TABLE 12

Testing of the influence of the filter plate on recovery

Reaction Conditions for Generating Starting Materials

| | |
|---|---|
| Equipment | ThermoMixer Equipped with a PCR Adapter |
| Sample | 200 uL Hu IgG$_1$ (varying concentration) |
| Digest Settings | 80° C., 1400 RPM |
| Time | 1 hour |
| Digest Buffer | Buffer A, 0.1% BSA |
| Wash Buffer | Buffer A, 0.1% BSA |
| WB Volume | 200 uL |
| Resin Amount | 15 uL |

LCMS Conditions Used for Analysis of Recovery

| | |
|---|---|
| Injection Volume | 5 uL |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK(SEQ. ID. NO. 5) - 937.74/836.43 |

| | Analyte Response (Area Counts) | Percent Loss (%) |
|---|---|---|
| GHP filterplate into LoBind Collection Plate Sample 0 | 20857 | |
| GHP filterplate into LoBind Collection Plate Sample 6 | 18934 | 9 |

Finally, filter plates from various suppliers were evaluated for recovery (Table 13). While there were variations between suppliers of filter plates using the same materials, PTFE provided the best overall recovery of materials screened.

TABLE 13

Screening of various filter plates for recovery

| | Sample Loss (%) between Sample 0 and Sample 6 | |
|---|---|---|
| | m/z = 937 | m/z = 603 |
| Polypropylene Plate 1 | 30 | 99 |
| Polypropylene Plate 1 | 10 | 66 |
| Polypropylene Plate 3 | 6 | 27 |
| GHP Plate | 1 | 33 |
| Polytetrafluoroethylene (PTFE) Plate | 0 | 25 |

Figure 13:
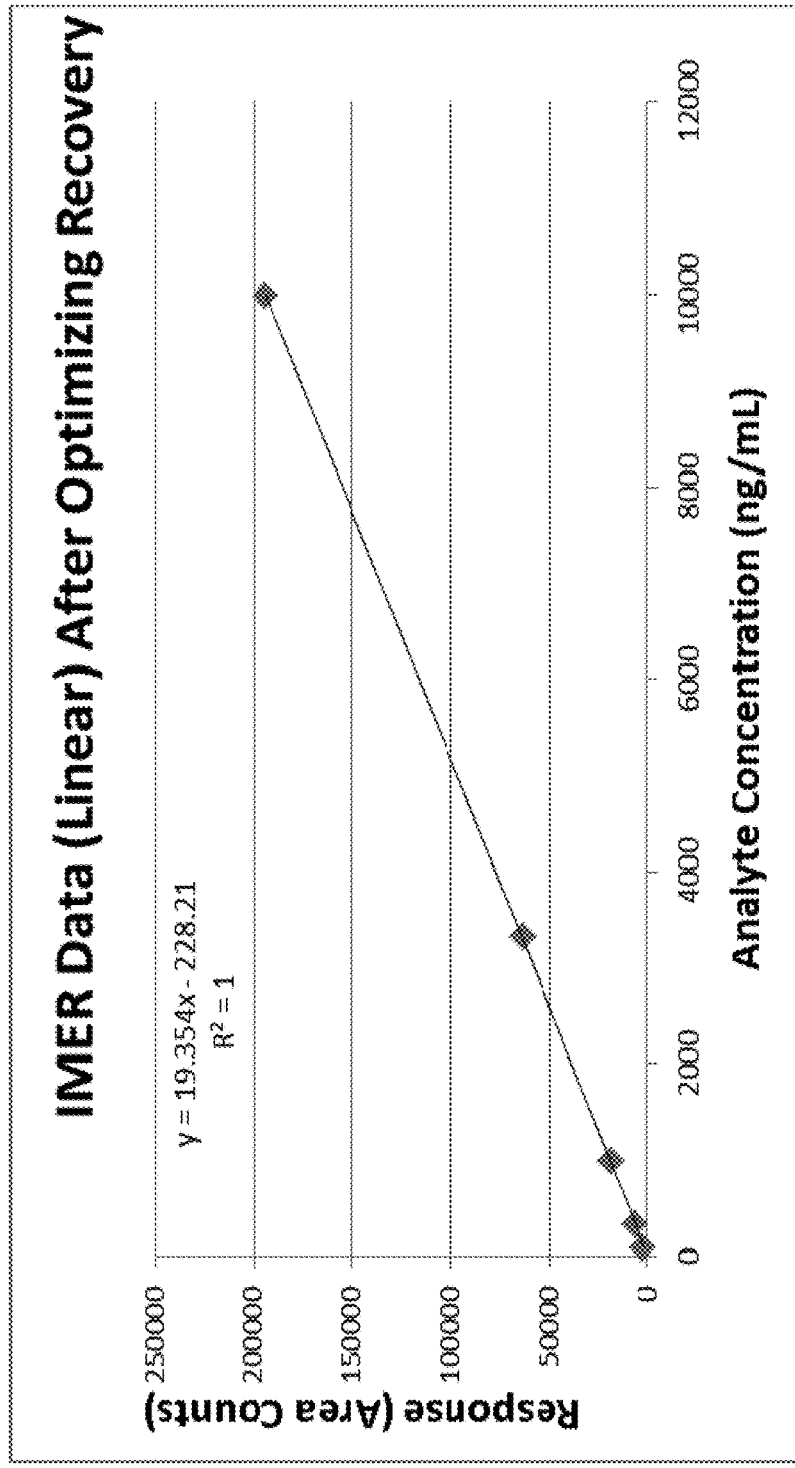
FIG. 13: IMER Linear Recovery Data after System Improvement.

Example 17: Use of PCR Tubes and Optimized Recovery Conditions Produces Linearity and Reproducibility In this example, the immobilized enzyme reactor with improved recovery is further tested for linearity and reproducibility. For this example the immobilized enzyme was prepared according to Example 2 and packed in a strip of 8 format prepared according to Example 9. Following incubation at 70° C. for 1 hour samples and the immobilized enzyme were placed into a GHP filter plate. Positive pressure was applied and the samples collected in a collection plate. The results are summarized below in Table 14 showing reproducibility. Plotting indicates the linearity of recovery is improved as shown in Table 15 and FIG. 13.

TABLE 14

Testing of reproducibility using PCR tubes and optimized recovery conditions

| Reaction Conditions | |
|---|---|
| Equipment | ThermoMixer Equipped with a PCR Adapter |
| Sample | 200 uL Hu IgG$_1$ (varying concentration) |
| Digest Settings | 80° C., 1400 RPM |
| Time | 1 hour |
| Digest Buffer | Buffer A, 0.05% BSA |
| Wash Buffer | Buffer A, 0.05% BSA |
| WB Volume | 200 uL |
| Resin Amount | 15 uL |
| LCMS Conditions Used for Analysis of Recovery | |
| Injection Volume | 10 uL |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK (SEQ. ID. NO. 5) - 937.74/836.43 |

| Sample | Analyte Response (Peak Area) |
|---|---|
| Sample 1 | 43852 |
| Sample 2 | 36866 |
| Sample 3 | 39394 |
| Sample 4 | 35691 |
| Sample 5 | 38908 |
| Sample 6 | 39002 |
| Average | 38952 |
| StDev | 2800 |
| CV (%) | 7.2 |

Linearity under improved conditions was also tested as indicated in Table 15.

TABLE 15

Testing of linearity using PCR tubes and optimized recovery conditions

| Reaction Conditions | |
|---|---|
| Equipment | ThermoMixer Equipped with a PCR Adapter |
| Sample | 200 uL Hu IgG$_1$ (varying concentration) |
| Digest Settings | 80° C., 1400 RPM |
| Time | 1 hour |
| Digest Buffer | Buffer A, 0.05% BSA |
| Wash Buffer | Buffer A, 0.05% BSA |
| WB Volume | 200 uL |
| Resin Amount | 15 uL |
| LCMS Conditions Used for Analysis of Recovery | |
| Injection Volume | 10 uL |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK (SEQ. ID. NO. 5) - 937.74/836.43 |

| Analyte (IgG1) Concentration (ng/mL) | Analyte Response (Area Counts) |
|---|---|
| 100 | 2404 |
| 333 | 6141 |
| 1000 | 18939 |
| 3333 | 63604 |
| 10000 | 193547 |

Example 18: Operation of Immobilized Enzyme Reaction in Static State

In this example, we have shown with the immobilized enzyme reactor and the working conditions used in Example 2 and 3, it is possible, under certain conditions, to remove the procedure of agitation of the enzyme-sample mix but still achieve sufficient enzyme reaction and product recovery.

Historically, shaking has been performed thinking it improved immobilized enzyme-sample interactions. However, testing of digestion under static conditions resulted in very good reproducibility and signal intensity suggesting that a very effective reaction was occurring in the absence of agitation. Table 16 shows immobilized enzyme reactor is able to produce consistent work product at static conditions.

TABLE 16

Testing of IMER reproducibility during static incubation

| Reaction Conditions | |
|---|---|
| Equipment | ThermoMixer Equipped with a PCR Adapter |
| Sample | 200 uL Hu IgG$_1$ (varying concentration) |
| Digest Settings | 80° C., Static |
| Time | 1 hour |
| Digest Buffer | Buffer A, 0.05% BSA |
| Wash Buffer | Buffer A, 0.05% BSA |
| WB Volume | 200 uL |
| Resin Amount | 15 uL |
| LCMS Conditions Used for Analysis of Recovery | |
| Injection Volume | 10 uL |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK(SEQ. ID. NO. 5) - 937.74/836.43 |

| Sample | Analyte Response (Area Counts) |
|---|---|
| Sample 1 | 46085 |
| Sample 2 | 49584 |
| Sample 3 | 50508 |
| Sample 4 | 48141 |
| Sample 5 | 51097 |
| Sample 6 | 46916 |
| Sample 7 | 48710 |
| Sample 8 | 50642 |
| Average | 48960 |
| StDev | 1827 |
| CV (%) | 3.7 |

Following this experiment, a test of across the plate uniformity was performed. In this experiment an Eppendorf ThermoMixer instrument outfitted with a PCR adapter was used. This plate adapter has 96 wells with 8 wells down by 12 across. In order to test across the plate uniformity a strip of 8 samples was placed on left side of the plate and the results were compared to a strip of 8 samples placed on the right side of the plate. The results in Table 17 suggested there was a significant difference in temperature between the two positions.

TABLE 17

Initial testing of across the plate reproducibility using a ThermoMixer outfitted with a PCR tube holder

| Reaction Conditions | |
|---|---|
| Equipment | ThermoMixer Equipped with a PCR Adapter |
| Sample | 200 uL Hu IgG$_1$ (varying concentration) |
| Digest Settings | 80° C., Static |
| Time | 1 hour |
| Digest Buffer | Buffer A, 0.05% BSA |

TABLE 17-continued

Initial testing of across the plate reproducibility using a
ThermoMixer outfitted with a PCR tube holder

| | |
|---|---|
| Wash Buffer | Buffer A, 0.05% BSA |
| WB Volume | 200 uL |
| Resin Amount | 15 uL |
| LCMS Conditions Used for Analysis of Recovery | |
| Injection Volume | 5 uL |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK(SEQ. ID. NO. 5) - 937.74/836.43 |

| | Analyte Response (Area Counts) | |
|---|---|---|
| Sample | Left side | Right Side |
| Sample 1 | 17595 | 15599 |
| Sample 2 | 18007 | 16211 |
| Sample 3 | 19120 | 15463 |
| Sample 4 | 21317 | 14356 |
| Sample 5 | 20060 | 14811 |
| Sample 6 | 19789 | 13337 |
| Sample 7 | 18987 | 13567 |
| Sample 8 | 14941 | 12958 |
| Average | 18727 | 14538 |
| StDev | 1926 | 1181 |
| CV(%) | 10.3 | 8.1 |
| Left Side Average | 18727 | |
| Right Side Average | 14538 | |
| Percent Difference (%) | 16.1 | |

The ability to obtain reproducible robust digestion without shaking enables this IMER format to be compatible with PCR equipment. PCR equipment has been optimized for reproducibility. By enabling compatibility with this instrumentation these advances resulted in an improvement in across the plate reproducibility.

TABLE 18

Testing of across the plate reproducibility using a PCR instrument

| Reaction Conditions | |
|---|---|
| Equipment | AR Veriti PCR Instrument |
| Sample | 200 uL Hu IgG$_1$ (1 ug/mL) |
| Digest Settings | 70° C., 1400 RPM |
| Time | 1 minute |
| Digest Buffer | 50 mM Tris, 100 mM CaCl$_2$ |
| Resin Amount | 15 uL |
| Injection Volume | 5 uL |

| Sample | | Hu IgG$_1$ |
|---|---|---|
| Reversed Phase A | 2% ACT (aq) 0.1% Formic Acid | |
| Reversed Phase B | 90% ACN (aq) 0.1% Formic Acid | |
| Reversed Phase Gradient | 2-70% B in 5 minutes at 500 uL/min | |
| UV/Vis | 214 nM | |

| | Analyte Response (Area Counts) | |
|---|---|---|
| Sample | Left side | Right Side |
| Sample 1 | 10084 | |
| Sample 2 | 9472 | 8230 |
| Sample 3 | 8190 | 7605 |
| Sample 4 | 8441 | 8271 |
| Sample 5 | 8200 | 8453 |
| Sample 6 | 8926 | 8539 |
| Sample 7 | 9008 | 8762 |

TABLE 18-continued

Testing of across the plate reproducibility using a PCR instrument

| | | |
|---|---|---|
| Sample 8 | 10253 | 9704 |
| Average | 9072 | 8626 |
| StDev | 805 | 678 |
| CV (%) | 8.9 | 7.9 |
| Left Side Average | 9072 | |
| Right Side Average | 8626 | |
| Percent Difference (%) | 3.3 | |

Following the validation of across the plate uniformity using the PCR thermo cycler as a heating device, a ThermoMixer C was tested for across the plate uniformity. As opposed to using a PCR bolt on adapter as was the case with the standard ThermoMixer, the ThermoMixer C came with a PCR attachment that enable better contact of the heat source with the samples.

TABLE 19

Follow-up testing of across the plate reproducibility using a ThermoMixer outfitted with fit for purpose PCR heating element

| Reaction Conditions | |
|---|---|
| Equipment | ThermoMixer C |
| Sample | 100 uL Hu IgG$_1$ (varying concentration) |
| Digest Settings | 70° C., 1600 RPM |
| Time | 1 hour |
| Digest Buffer | Buffer A. 0.05% BSA |
| Wash Buffer | Buffer A, 0.05% BSA |
| WB Volume | 200 uL |
| Resin Amount | 15 uL |
| LCMS Conditions Used for Analysis of Recovery | |
| Injection Volume | 5 uL |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK (SEQ. ID. NO. 5) - 937.74/836.43 |

| Sample IgG1 Concentration in ng/mL | Analyte Response (Area Counts) | | Percent Difference (%) |
|---|---|---|---|
| | Left Side | Right Side | |
| 50 | 485 | 474 | 2.3 |
| 158 | 1548 | 1488 | 4.0 |
| 500 | 4656 | 4492 | 3.6 |
| 1580 | 15183 | 14722 | 3.1 |
| 5000 | 48399 | 49428 | -2.1 |
| 15800 | 132284 | 145160 | -9.3 |
| 50000 | 421340 | 448437 | -6.2 |

Example 19: Increased Calcium Concentration has Positive Effect on Trypsin Digestion in IMER Briefly, an IMER was created adding 15 uL of immobilized enzyme slurry prepared to the bottom of a 300 uL, strip of 8 PCR tubes. Samples were added directly to this slurry without pretreatment (neither reduction nor alkylation were employed). Samples were heated using a PCR thermo cycler. Following incubation the entire sample is removed using a multichannel pipette and transferred to a filter plate. A collection plate was placed below the filter plate and positive pressure was applied separating the immobilized enzyme from the digested sample.

Human, monoclonal IgG1 was used in this experiment. The digestion efficiency was measured via measurement of peak area corresponding to the two peptides VVSVLTVL-HQDWLNGK (SEQ ID NO 4) and TTPPVLDSDGSFF-LYSK (SEQ ID NO 5). These two peptides are unique to human IgG. Table 20 shows the two different IgG peptides that are digested by trypsin and how they responded to various $CaCl_2$ concentrations in the reaction buffer.

TABLE 20

Exemplary human IgG peptide digestion efficiency in response to calcium concentration Native IgG Peak Response as a Function of $CaCl_2$ Concentration and Digestion Time

| Time (min) | $CaCl_2$ Concentration mmol | | | | | | | |
|---|---|---|---|---|---|---|---|---|
| | 0 | 10 | 20 | 60 | 110 | 260 | 500 | 1000 |
| Peptide m/z - 937 | | | | | | | | |
| 5 | 1406 | 869 | 3028 | 4155 | 4732 | 5378 | 6222 | 4796 |
| 15 | 1703 | 3882 | 5282 | 5851 | 6571 | 7300 | 7555 | 7175 |
| 30 | 1997 | 4441 | 5494 | 6924 | 7234 | 7869 | 8595 | 7832 |
| 45 | 2128 | 5150 | 6678 | 7222 | 7893 | 8362 | 8539 | 8261 |
| 60 | 2269 | 5059 | 7238 | 8122 | 8218 | 8964 | 8134 | 8785 |
| 75 | 2244 | 5466 | 8181 | 8314 | 7819 | 8596 | 8904 | 8629 |
| 90 | 2423 | 5372 | 7788 | 9140 | N/A | 9291 | 9265 | 8784 |
| Peptide m/z - 603 | | | | | | | | |
| 5 | 892 | 773 | 1095 | 1725 | 2160 | 1833 | 1441 | 434 |
| 15 | 1182 | 1360 | 2094 | 2533 | 3261 | 2766 | 2355 | 1192 |
| 30 | 1355 | 1621 | 1989 | 2988 | 3360 | 2977 | 2766 | 1787 |
| 45 | 1350 | 1924 | 2484 | 2900 | 3565 | 2988 | 2710 | 1991 |
| 60 | 1537 | 2011 | 2688 | 3700 | 3528 | 3340 | 2577 | 2037 |
| 75 | 1670 | 2097 | 2836 | 3869 | 3313 | 3195 | 2849 | 2192 |
| 90 | 1821 | 2083 | 2972 | 3844 | N/A | 3266 | 2901 | 2315 |

The new finding was that increasing the concentration of $CaCl_2$ beyond the established concentration range can have a dramatic impact on analyte response and enzyme activity. Contrary to the established literature that "calcium chloride used in concentrations above 1 mM has shown no additional benefit in improving enzyme stability" (Promega Technical Manual #9PIV511; Sipos and Merkel. 1970. An Effect of Calcium Ions on the Activity, Heat Stability, and Structure of Trypsin. Biochemistry 9:2766-2775), in the format of Immobilized Enzyme Reactors (IMERs), the increased concentration of calcium chloride above 1 mM has been shown to increase enzyme efficiency, measured by the two peak peptides unique to human IgG digestion by trypsin.

Figure 14:
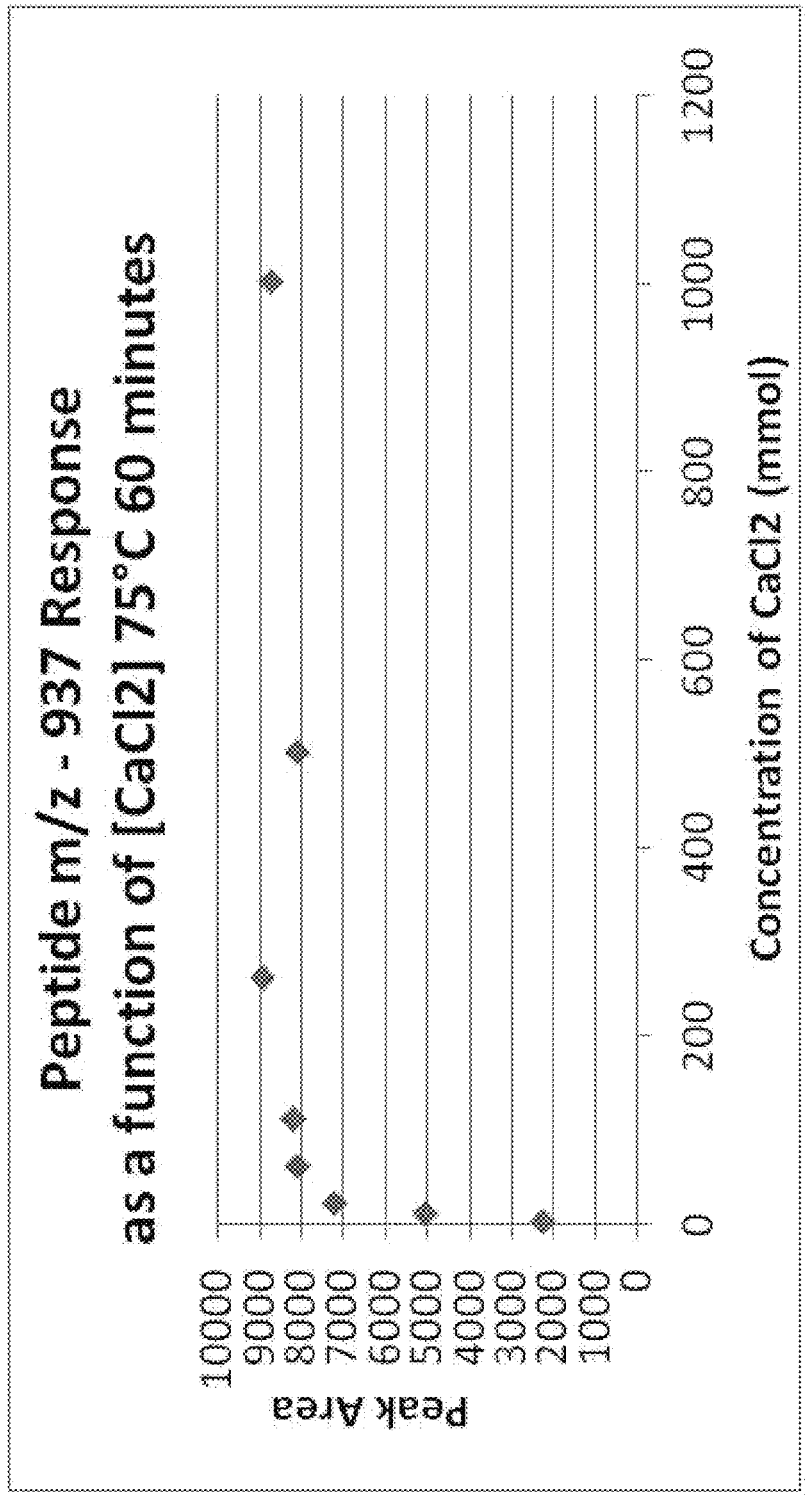
FIG. 14: Exemplified plotting points of human IgG peptide m/z=937 at various CaCl2 concentrations, captured for 60 minute digestion at elevated temperature of 75° C.
Figure 15:
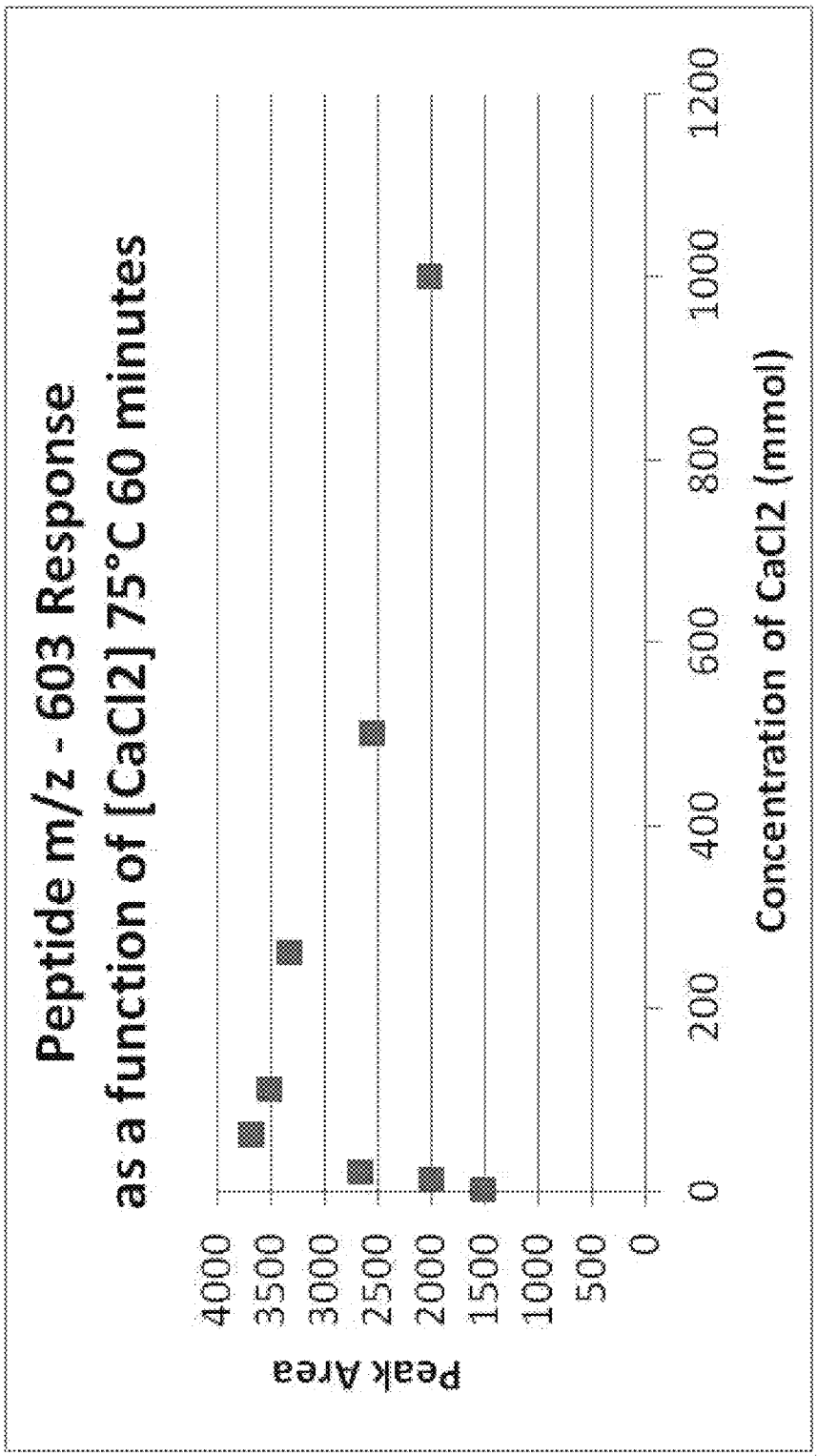
FIG. 15: Exemplified plotting points of human IgG peptide m/z=603 at various CaCl2 concentrations, captured for 60 minute digestion at elevated temperature of 75° C.
Figure 16:
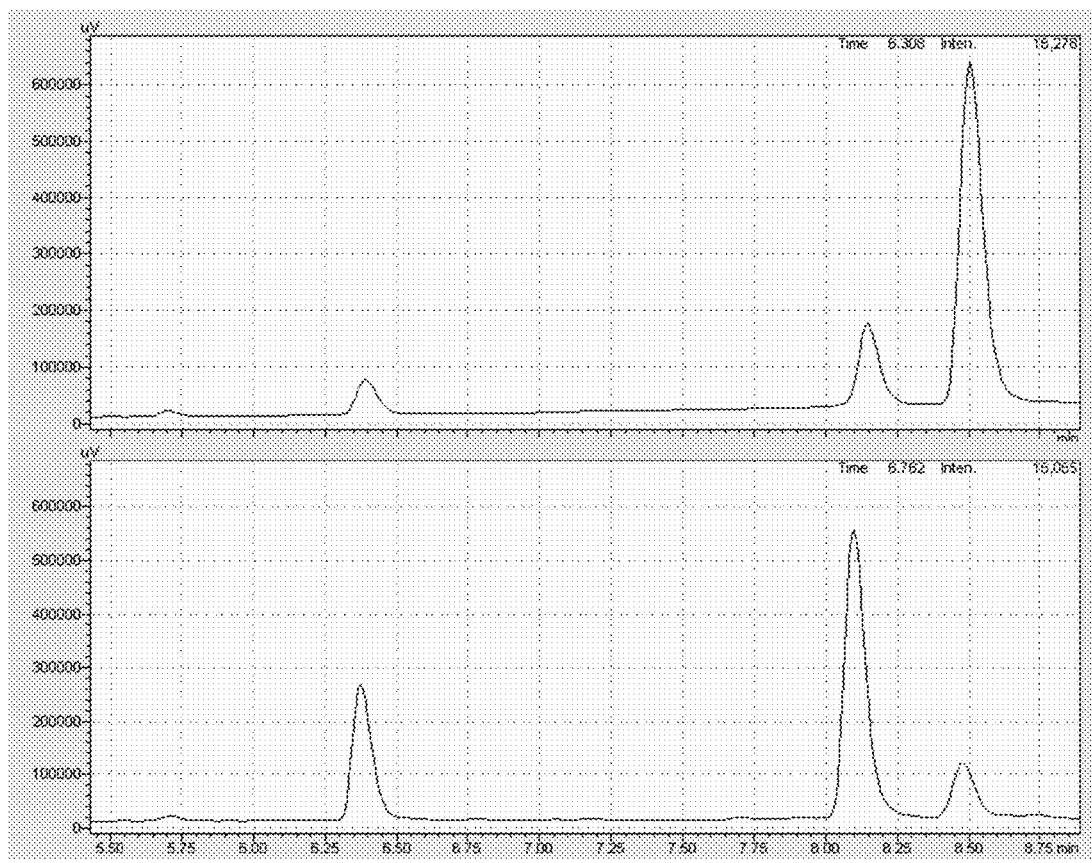
FIG. 16: A comparison of insulin digest efficiency using varying concentrations of CaCl2. Both: Immobilized enzyme prepared according to Example 2, packed in a strip of 8 format prepared according to Example 9. Top: Insulin digested using 50 mM TBS. Bottom: Insulin digested using 50 mM TBS and 100 mM $CaCl_2$.

For the 2 peptides we have been monitoring for IgG in this example, under elevated temperatures (75° C.), one peptide, m/z 937, reaches an asymptote at much higher concentration of $CaCl_2$ (260 mM and 60 minutes of digestion, see FIG. 14, the exemplified plotting points at various $CaCl_2$ concentrations, captured at 60 minute digestion based on table 20 chart). The other peptide, m/z 603, peaks at the lower concentration of 60 mM and 60 minute digestion, then it declines (see FIG. 15, the exemplified plotting points at various $CaCl_2$ concentrations, captured for 60 minute digestion based on table 20 chart). Most protocols recommend 10 mM-20 mM $CaCl_2$ for trypsin digestion, but it is obvious such low concentrations of calcium are insufficient for IMER digestions under these conditions. This is a surprising departure from the commonly accepted notion that "when the concentration of calcium was increased from $10^{-6}M$ to $10^{-3}M$, enzyme activity increased. There is no further increase in the enzymatic activity of trypsin beyond $10^{-3}M$ calcium" (Sipos and Merkel. 1970. An Effect of Calcium Ions on the Activity, Heat Stability, and Structure of Trypsin. Biochemistry 9:2766-2775).

Example 20: Buffer Screening

Using insulin as a model protein a significant number of buffer conditions were screened.

Digestion was performed using an immobilized enzyme prepared according to Example 2 that was packed in a strip of 8 format prepared according to Example 9. Briefly, a 5 mg sample of USP standard human insulin was dissolved in 2% acetic acid, 100 mM glycine to a concentration of 10 mg/mL. This solution was then diluted 100 fold into digest buffer. The digest buffer varies according to the descriptions in Table 21. 200 uL of this sample was added to each of 2 wells of immobilized enzyme prepared according to Example 2 and packed in a strip of 8 format prepared according to Example 9. Each sample was digested for 60 seconds at 70° C. using a Veriti Thermo Cycler, removed from the instrument and allowed to cool for 5 minutes. Once all of the samples had cooled the 2 samples from each buffer condition were pooled, centrifuged and the digest materials decanted. These materials were analyzed by LC-UV/Vis according to parameters in Table 21 below.

TABLE 21

Conditions used for the analysis of insulin samples digested in various buffers

| | |
|---|---|
| Sample | 100 ug/mL digested Hu insulin |
| Injection Volume | 25 uL |
| Digest Conditions | 70° C., 60 seconds |
| Reversed Phase A | 2% ACN (aq) 0.1% Trifluoroacetic Acid |
| Reversed Phase B | 90% ACN (aq) 0.1% Trifluoroacetic Acid |
| Reversed Phase Gradient | 2-70% B in 7 minutes |
| UV/Vis | 214 nm |

Results are summarized in Table 22. Concentration of buffer and salt had minimal impact while the concentration of $CaCl_2$ impacted results dramatically. An increase in digestion was observed using concentrations of CaCl2 as high as 500 mM.

TABLE 22

Screening effect of buffer composition on digestion in novel immobilized enzyme reactor

| [Tris Buffer] (M) | [NaCl] (M) | [CaCl2] (M) | [Gdn-HCl] (M) | Peptide | Digested Protein | Undigested |
|---|---|---|---|---|---|---|
| 0.05 | 0.15 | 0.1 | 0.5 | 312708 | 775531 | 3451883 |
| 0.05 | 0.15 | 0.1 | 1 | 251672 | 628822 | 3485374 |
| 0.05 | 0.15 | 0.1 | 2 | 144781 | 358197 | 3654560 |
| 0.05 | 0.15 | 0.1 | 4 | 48310 | 121687 | 3965888 |
| 0.05 | 0.15 | 0.1 | 6 | 4037 | 10024 | 3588624 |
| 0.05 | 0.15 | 0.1 | 0 | 666300 | 1673510 | 1997976 |
| 0.1 | 0.15 | 0.1 | 0 | 757366 | 1905200 | 1690545 |
| 0.25 | 0.15 | 0.1 | 0 | 812930 | 2040515 | 1518493 |
| 0.5 | 0.15 | 0.1 | 0 | 725445 | 1841728 | 1757516 |
| 1 | 0.15 | 0.1 | 0 | 557101 | 1414687 | 2363160 |
| 0.05 | 0.1 | 0.1 | 0 | 735107 | 1849499 | 1856365 |
| 0.05 | 0.25 | 0.1 | 0 | 641281 | 1624802 | 2010244 |
| 0.05 | 0.5 | 0.1 | 0 | 595743 | 1523214 | 2277385 |
| 0.05 | 1 | 0.1 | 0 | 505382 | 1326371 | 2483952 |
| 0.05 | 2 | 0.1 | 0 | 485840 | 1234885 | 2034464 |
| 0.05 | 0.15 | 0 | 0 | 140971 | 334592 | 3882030 |
| 0.05 | 0.15 | 0.05 | 0 | 762653 | 1825058 | 1792154 |
| 0.05 | 0.15 | 0.1 | 0 | 854883 | 2054809 | 1357977 |
| 0.05 | 0.15 | 0.25 | 0 | 921304 | 2234833 | 944875 |
| 0.05 | 0.15 | 0.5 | 0 | 965752 | 2502880 | 640661 |
| 0.05 | 0.15 | 1 | 0 | 674100 | 1746017 | 1584887 |

As Table 22 indicates, digestion efficiency as a function of calcium chloride was in order 500 mM>250 mM>100 mM>50 mM>1M>0 mM. Although it is not clear what makes increased CaCl2 concentration associate with higher trypsin digestion efficiency, it is clear that the higher concentration of CaCl2 has a synergistic effect on trypsin digestion, for at least human IgG in Example 17 and human insulin in this example.

It is contemplated that other metal ions may have a similar effect on enzyme at elevated temperature. For example, $Na^+$, $Mg^{2+}$, $Ca^{2+}$, $Sr^{2+}$, $Mn^{2+}$, $Co^{2+}$, $Ni^{2+}$, $Zn^{2+}$, $Cu^{2+}$, $Fe^{3+}$ in various buffer solutions with high ionic strength are expected to show temperature dependent increase in enzyme reaction. One non-limiting explanation is that the metal presence in the reaction buffer, especially in the IMER format enzyme reactions, dramatically increases the chances of enzyme to contact substrate by unknown means. Another non-limiting explanation of the metal effect in the reaction buffer is that the enzyme may be transformed by the presence of metal to become a more active format, such as undergoing conformational change to have altered Kcat/Km ratio that favors higher reaction efficiency. Regardless, it is a surprising discovery from this disclosure that metal concentration can be revised further from the currently available art and protocols to improve the enzyme reaction efficiency at elevated temperatures.

Example 21: High $CaCl_2$ Concentration in Solution Based Enzyme Reaction System With the surprising result of high concentration of $CaCl_2$ effect on immobilized enzyme reactor, exemplified in Example 17 and Example 18, it is contemplated that the metal cations have a similar effect on solution based enzyme reactions.

In this example, the enzyme and substrate are mixed in a uniformly heated reaction vessel, including but not limited to a PCR tube or multi-well plate that is fit for high throughput reactions. The ratio of the enzyme to the substrate is controlled above the traditional 1:50, preferably at a ratio exceeding 1:20. Contrary to the traditional literature and the established protocols that set the $CaCl_2$ concentration in the final reaction buffer no more than 1 mM, the $CaCl_2$ or any other metal cations in these solution based enzyme reactions is adjusted to more than 1 mM, sometimes at molarities greater than or equal to 100 mM, to achieve an efficacious digestion.

An exemplified enzyme in this solution based enzyme reactor system is trypsin, and its substrate can be human IgG or human insulin in digestion conditions described above. The temperature can be set at above 37° C. or below 37° C. Other cations, such as $Na^+$, $Mg^{2+}$, $Ca^{2+}$, $Sr^{2+}$, $Mn^{2+}$, $Co^{2+}$, $Ni^{2+}$, $Zn^{2+}$, $Cu^{2+}$, $Fe^{3+}$ in various buffer solutions with high ionic strength are expected to show positive enzyme reaction effects.

Example 22: Digestion of Carbonic Anhydrase without Pretreatment

Carbonic Anhydrase is a 29 kilodalton (kD), hydrophobic protein. 200 uL samples at a concentration of 100 ug/mL were digested using various digestion times and immobilized enzyme prepared according to Example 2 that was packed in a strip of 8 format prepared according to Example 9. The digestion buffer was 50 mM TBS with 100 mM $CaCl_2$. Digestion occurred at 70° C. in a PCR thermo cycler. Following digestion the products were separated by reversed phase chromatography and analyzed by UV at 214 nm.

TABLE 23

Conditions used for the analysis of digested Carbonic Anhydrase

| | |
|---|---|
| Sample | 100 ug/mL digested Carbonic Anhydrase |
| Injection Volume | 15 uL |
| Reversed Phase A | 2% ACN (aq) 0.1% Trifluoroacetic Acid |
| Reversed Phase B | 90% ACN (aq) 0.1% Trifluoroacetic Acid |
| Reversed Phase Gradient | 2-50% B in 60 minutes |
| UV/Vis | 214 |

Figure 17:
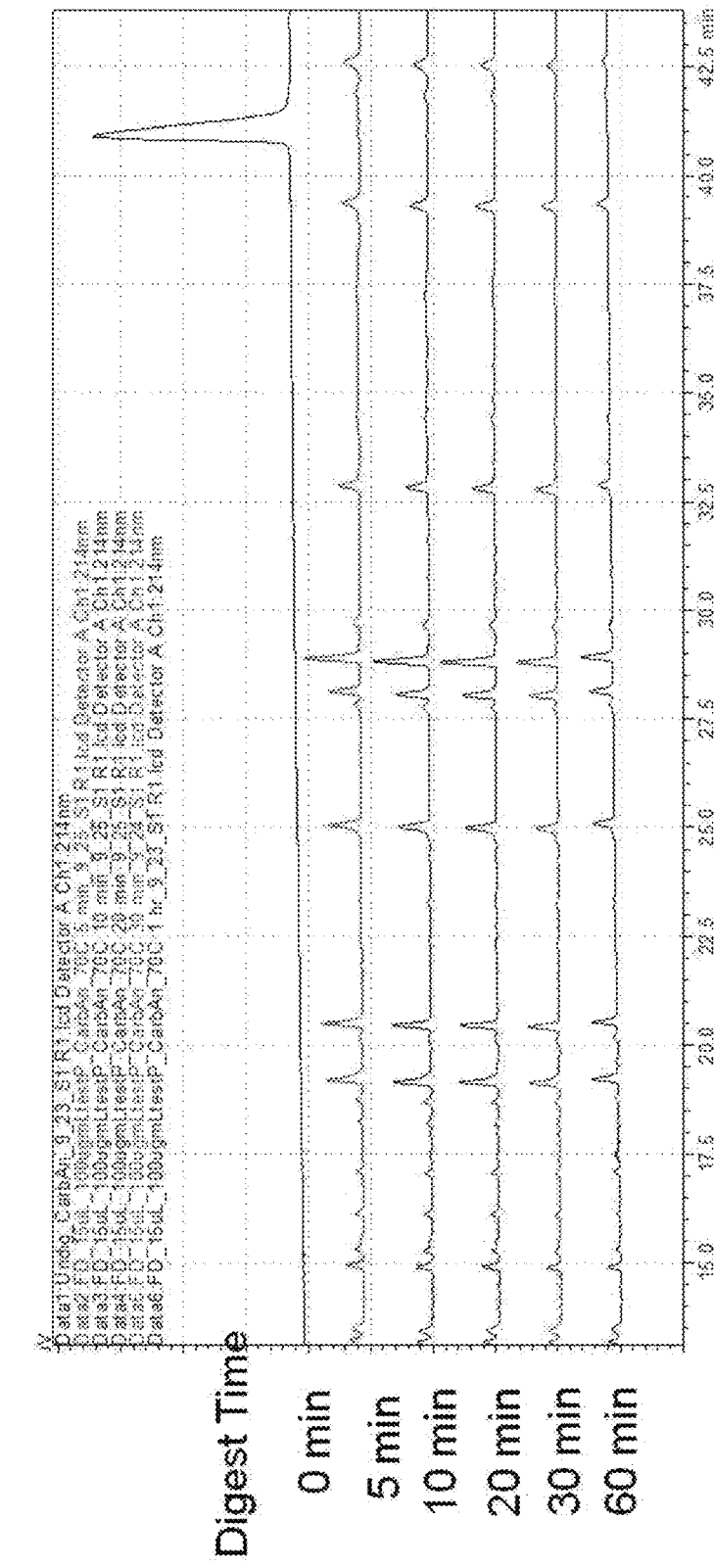
FIG. 17: Digestion of Carbonic Anhydrase without pretreatment using immobilized enzyme prepared according to Example 2, packed in a strip of 8 format prepared according to Example 9. Carbonic Anhydrase is a 29 kilodalton (kD), hydrophobic protein.

No undigested material was present after a 5 minute digestion time. A summary of results is also presented in FIG. 17

Example 23: Digestion of Bovine Serum Albumin (BSA) without Pretreatment

For this example the immobilized enzyme was prepared according to Example 2 and packed in a strip of 8 format prepared according to Example 9. BSA is a 66 kD, hydrophobic protein with 15 disulfide bonds. 200 uL samples at a concentration of 100 ug/mL were digested using various digestion times and immobilized enzyme prepared according to Example 2 that was packed in a strip of 8 format prepared according to Example 9. The digestion buffer was 50 mM TBS with 100 mM $CaCl_2$. Digestion occurred at 70° C. in a PCR thermo cycler. Following digestion the products were separated by reversed phase chromatography and analyzed by UV at 214 nm.

TABLE 24

Conditions used for the analysis of digested BSA

| | |
|---|---|
| Sample | 100 ug/mL digested BSA |
| Injection Volume | 15 uL |
| Reversed Phase A | 2% ACN (aq) 0.1% Trifluoroacetic Acid |
| Reversed Phase B | 90% ACN (aq) 0.1% Trifluoroacetic Acid |
| Reversed Phase Gradient | 2-50% B in 60 minutes |
| UV/Vis | 214 |

Figure 18:
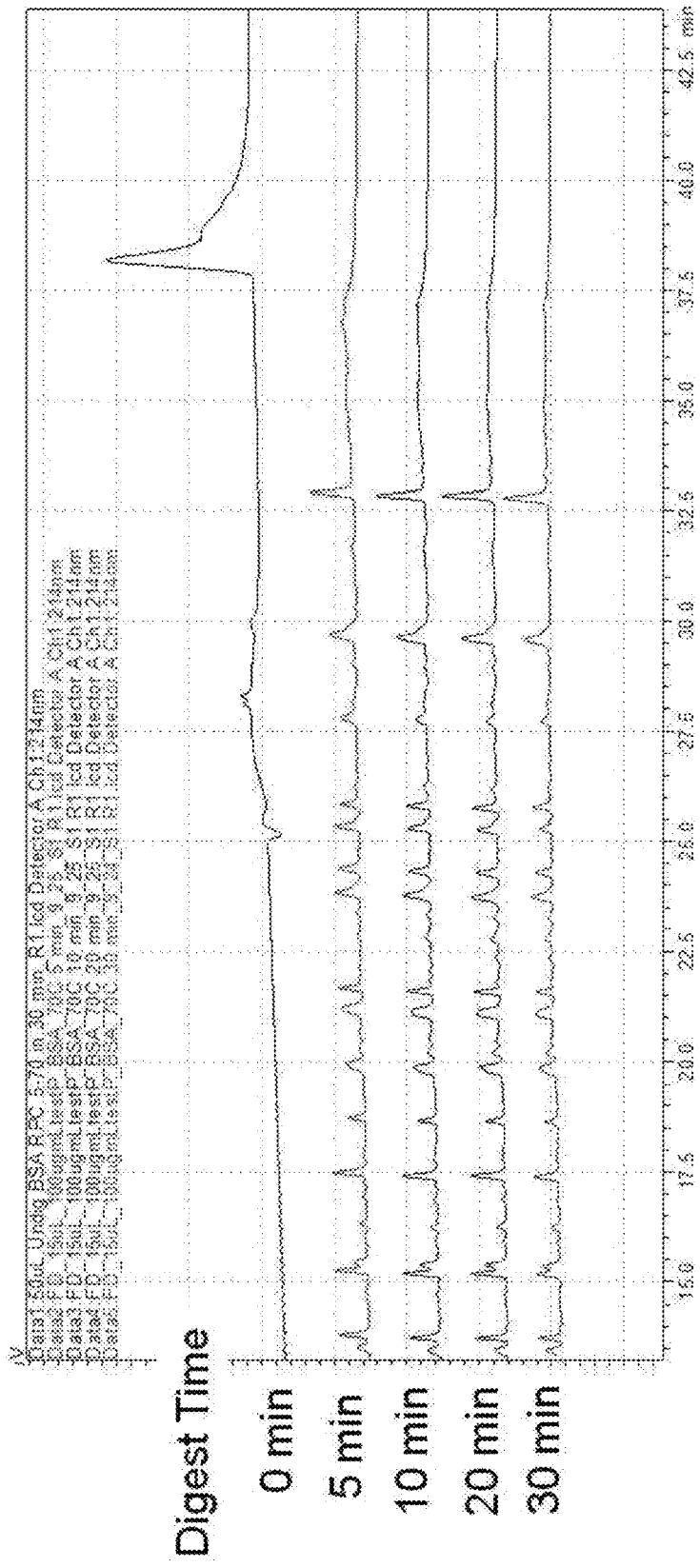
FIG. 18: Digestion of Bovine Serum Albumin (BSA) without pretreatment using immobilized enzyme prepared according to Example 2, packed in a strip of 8 format prepared according to Example 9. BSA is a 66 kD, hydrophobic protein with 15 disulfide bonds.

No undigested material was present after a 5 minute digestion time. A summary of results is also presented in FIG. 18

Example 24: Digestion of Ribonuclease a without Pretreatment Using Immobilized Enzyme For this example the immobilized enzyme was prepared according to Example 2 and packed in a strip of 8 format prepared according to Example 9. Ribonuclease A is a 13.7 kD polar protein considered highly stable toward unfolding (Markel et al. 2001. Protein Engineering 14: 791-796). 200 uL samples at a concentration of 100 ug/mL were digested using various digestion times and immobilized enzyme prepared according to Example 2 that was packed in a strip of 8 format prepared according to Example 9. The digestion buffer was 50 mM TBS with 100 mM $CaCl_2$. Digestion occurred at 70° C. in a PCR thermo cycler. Following digestion the products were separated by reversed phase chromatography and analyzed by UV at 214 nm.

TABLE 25

Conditions used for the analysis of digested Ribonuclease A

| | |
|---|---|
| Sample | 100 ug/mL digested Ribonuclease A |
| Injection Volume | 15 uL |
| Reversed Phase A | 2% ACN (aq) 0.1% Trifluoroacetic Acid |

TABLE 25-continued

Conditions used for the analysis of digested Ribonuclease A

| | |
|---|---|
| Reversed Phase B | 90% ACN (aq) 0.1% Trifluoroacetic Acid |
| Reversed Phase Gradient | 2-50% B in 60 minutes |
| UV/Vis | 214 |

Figure 19:
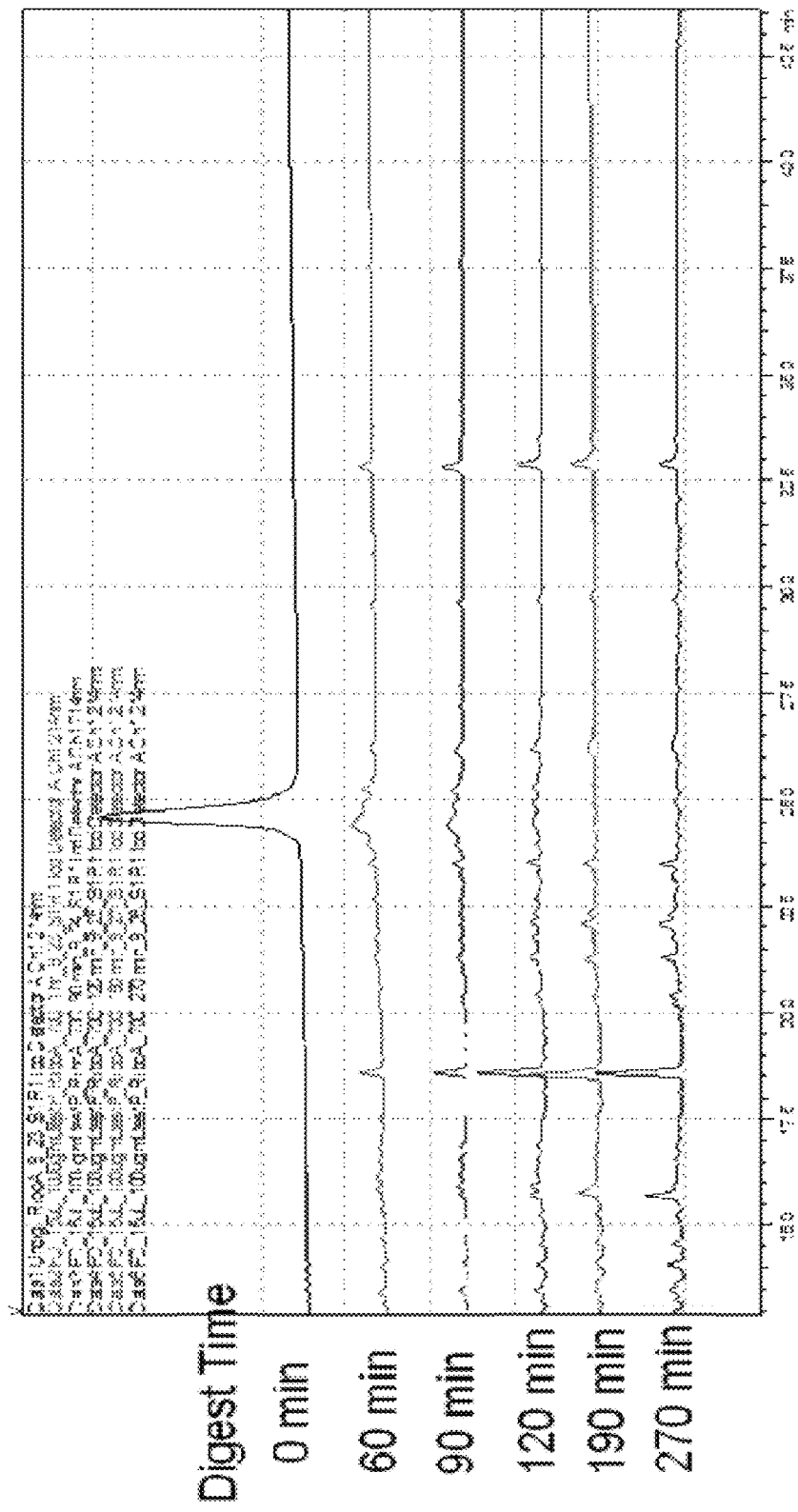
FIG. 19: Digestion of Ribonuclease A without pretreatment using immobilized enzyme prepared according to Example 2, packed in a strip of 8 format prepared according to Example 9. Ribonuclease A is 13.7 kD polar protein considered "highly stable toward unfolding." Protein Eng. (2001) 14: 791-796.
Figure 20:
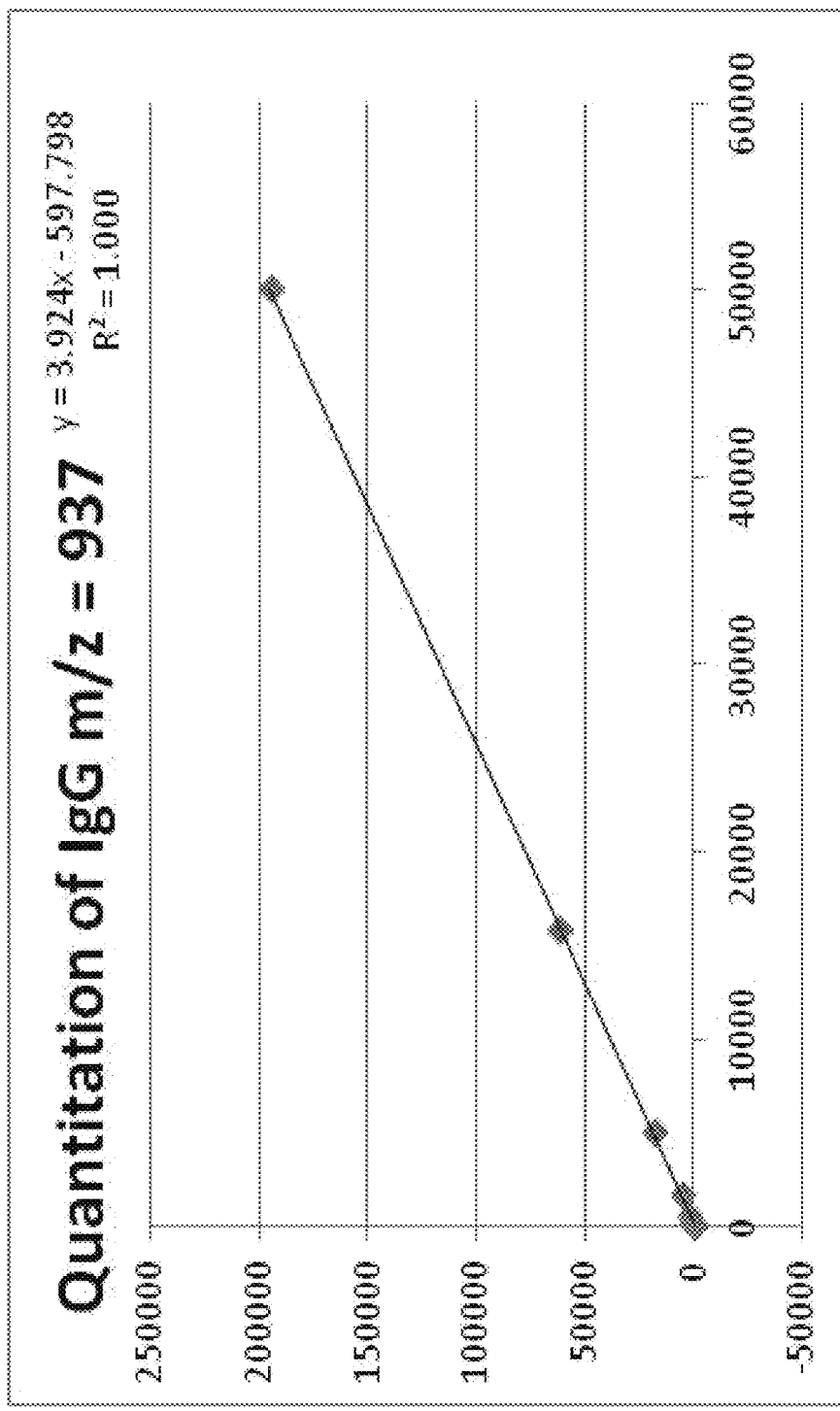
FIG. 20: Standard Curve of IgG in BSA without pretreatment using immobilized enzyme prepared according to Example 2, packed in a strip of 8 format prepared according to Example 9.

No undigested material was present after a 270 minute digestion time. A summary of results is also presented in FIG. 19

Example 25: Use of Various Additives to Aid in the Digestion Proteins at High Concentrations It was observed that when operated using conditions combining high temperatures with high protein concentrations, denaturation of proteins in the working solution could lead to aggregation. It was the goal of these experiments to find buffer conditions that would enable the direct digestion of up to 50 uL of blood plasma. A screen of various additives was performed using 12.5 mg/mL BSA as a model system. The final concentration of the additive is listed in Table 26 below. The starting buffer was comprised of 50 mM TBS, 100 mM $CaCl_2$. Samples comprised of 12.5 mg/mL BSA in buffer/additive mixture were added to immobilized enzyme was prepared according to Example 2 and packed in a strip of 8 format prepared according to Example 9 then incubated on a ThermoMixer C at 70° C. Aggregation was monitored as a function of time.

TABLE 26

A screen for the effect of additives on aggregation

| Additive | 30 min | 60 min | 90 min | 210 min |
|---|---|---|---|---|
| ACN[1] 1% | n | n | n | y |
| ACN 5% | s | s | s | y |
| ACN 10% | y | y | y | y |
| ACN 20% | y | y | y | y |
| IPA[2] 1% | n | n | n | y |
| IPA 5% | s | s | s | y |
| IPA 10% | y | y | y | y |
| IPA 20% | n | n | n | y |
| DMSO[3] 1% | n | n | n | y |
| DMSO 5% | n | n | n | n |
| DMSO 10% | n | n | n | s |
| DMSO 20% | y | y | y | y |
| MeOH[4] 1% | n | n | n | y |
| MeOH 5% | n | n | n | y |
| MeOH 10% | y | y | y | y |
| MeOH 20% | y | y | y | y |
| TFE[5] 1% | n | n | n | y |
| TFE 5% | y | y | y | y |
| TFE 10% | y | y | y | y |
| TFE 20% | y | y | y | y |
| Formamide 1% | n | n | n | y |
| Formamide 5% | n | n | n | y |
| Formamide 10% | n | n | n | n |
| Formamide 20% | n | n | n | n |
| DMF[6] 1% | n | n | n | y |
| DMF 5% | n | n | n | y |
| DMF 10% | y | y | y | y |
| DMF 20% | y | y | y | y |
| Guanidine HCl 0.5M | n | n | n | n |
| Tween 20 0.005% | y | y | y | y |
| Tween 20 0.05% | y | y | y | y |
| Glycerol 5% | n | n | n | n |
| Glycerol 10% | n | n | n | n |
| Octylglucoside | n | n | n | n |
| deoxycholate | y | y | y | y |

N = No aggregation
Y = Aggregation
S = Slight Aggregation
[1]ACN = acetonitrile,
[2]IPA = Isopropanol,
[3]DMSO = dimethylsulfoxide,
[4]MeOH = methanol,
[5]TFE = trifluoromethanol,
[6]DMF = dimethylformamide While various literature references describe the use of additives for the prevention of aggregation (Shiraki et al. 2003. Science and Technology of Advanced Materials 4:55-59; Shiraki et al. 2002. The Journal of Biochemistry 132: 591-595.) it is important to note the non-obviousness of these finding. While some additives have precedent as beneficial to the prevention of aggregation they were not beneficial for use in this working system. Also of note, it was observed that heating the sample in the presence of the immobilized enzyme decreased the propensity of the sample to aggregate. While not wishing to be limited to theory, it is possible the digestion of the sample from protein into more soluble peptides increases the overall solubility of the reaction mixture.

Following this initial study the additives identified at best preventing aggregation were further screened for their effect on activity.

Example 26: Screening for the Effect of Additives on IMER Activity

Using insulin as a model protein, buffers shown to prevent aggregation were screened for their effect on IMER activity.

Briefly, a 5 mg sample of USP standard human insulin was dissolved in 2% acetic acid, 100 mM glycine to a concentration of 10 mg/mL. This solution was then diluted 100 fold into digest buffer. The digest buffer varies according to the descriptions in Table 28. 200 uL of this sample was added to each of 2 wells of immobilized enzyme prepared according to Example 2 and packed in a strip of 8 format prepared according to Example 9. Each sample was digested for 60 seconds at 70° C. using a Veriti Thermo Cycler, removed from the instrument and allowed to cool for 5 minutes. Once all the samples had cooled the 2 samples from each buffer condition were pooled, centrifuged and the digest materials decanted. These materials were analyzed by LC-UV/Vis according to parameters in Table 27 below.

TABLE 27

Conditions used for the analysis of insulin samples digested in the presence of various additives

| | |
|---|---|
| Sample | 100 ug/mL digested Hu insulin |
| Injection Volume | 25 uL |
| Digest Conditions | 70° C., 60 seconds |
| Reversed Phase A | 2% ACN (aq) 0.1% Trifluoroacetic Acid |

TABLE 27-continued

Conditions used for the analysis of insulin samples digested
in the presence of various additives

| | |
|---|---|
| Reversed Phase B | 90% ACN (aq) 0.1% Trifluoroacetic Acid |
| Reversed Phase Gradient | 2-70% B in 7 minutes |
| UV/Vis | 214 nm |

Results are summarized in Table 28.

TABLE 28

Screening effect of additives on activity of
novel immobilized enzyme reactor

| Additive Percent (%) | Digestion as Percent of Initial (%) |
|---|---|
| Additive = Glycerol | |
| 0 | 100% |
| 5 | 83% |
| 10 | 65% |
| 20 | 36% |
| Additive = Octylglycoside | |
| 0 | 100% |
| 0.05 | 105% |
| 0.1 | 105% |
| 0.2 | 102% |
| Additive = DMSO | |
| 0 | 100% |
| 5 | 91% |
| 10 | 79% |
| 15 | 75% |
| Additive = Formamide | |
| 0 | 100% |
| 5 | 90% |
| 10 | 62% |
| 15 | 40% |
| 20 | 31% |

Further testing ruled out the use of DMSO. Use of this additive at effective concentrations for elimination of aggregation (e.g. 10%) failed to be effective in samples containing 50 uL feline serum. As a follow-up to these experiments, 150 uL 10%/glycerol, 0.1% Octylglycoside and 10% formamide in 50 mM TBS, 100 mM CaCl$_2$ were added 500 uL beagle plasma. These samples were incubated on a ThermoMixer C for 90 minutes. Following incubation samples comprised of 0.1% Octylglycoside and 10% formamide in 50 mM TBS, 100 mM CaCl$_2$ showed significant aggregation. Following incubation the sample comprised of 10% glycerol in 50 mM TBS, 100 mM CaCl$_2$ showed no aggregation. A follow-up to this experiment screened the effects of varied CaCl$_2$ concentrations (increased and decreased concentrations) in samples comprised of 50 uL beagle plasma in 10% glycerol in 50 mM TBS. Results showed optimal digestion efficiency at 500 mM CaCl$_2$.

Example 27: Quantitation of Human IgG in Monkey Plasma

It was observed that when operated at high protein loads denaturation of proteins in the working solution could lead to aggregation. In these cases it was determined that the addition of glycerol to a 10% final concentration and use of 500 mM CaCl$_2$ prevented the formation of aggregates while enabling rapid digestion under denaturing conditions. The results below demonstrate quantitation of human IgG in 50 uL monkey plasma diluted in 150 uL of 50 mM TBS, 500 mM CaCl$_2$, 10% glycerol, digestion by immobilized enzyme prepared according to Example 2 that was packed in a strip of 8 format prepared according to Example 9. Digestion occurred in 75 minutes using a ThermoMixer C operated at 70° C.

TABLE 29

Sample preparation and LC/MS parameters for the digestion and
analysis of human IgG$_1$ in 50 uL monkey plasma

| Reaction Conditions | |
|---|---|
| Equipment | Eppendorf ThermoMixer C |
| Sample | Varying concentrations human IgG in monkey plasma |
| Digest Settings | 70° C., 1600 RPM |
| Time | 75 minutes |
| Digest Buffer | 50 mM TBS, 500 mM CaCl$_2$, 10% glycerol |
| Diluent | 50 mM TBS, 100 mM CaCl$_2$ |
| Digest to Diluent ratio | 1:99 |
| Resin Amount | 15 uL |
| LCMS Conditions Used for Analysis | |
| Injection Volume | 5 uL of diluted sample |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK (SEQ. ID. NO. 5) - 937.74/836.43 |

TABLE 30

Calibration curves of human IgG1 in monkey plasma

| | IgG in Monkey Plasma Final IgG Concentration (ng/mL) | | | | |
|---|---|---|---|---|---|
| | 10 | 31.6 | 100 | 316 | 1000 |
| Peak Areas Front Curve | 32.22 | 128 | 450 | 1368 | 4238 |
| Peak Areas Back Curve | 20.48 | 139 | 442 | 1331 | 4495 |

Figure 21:
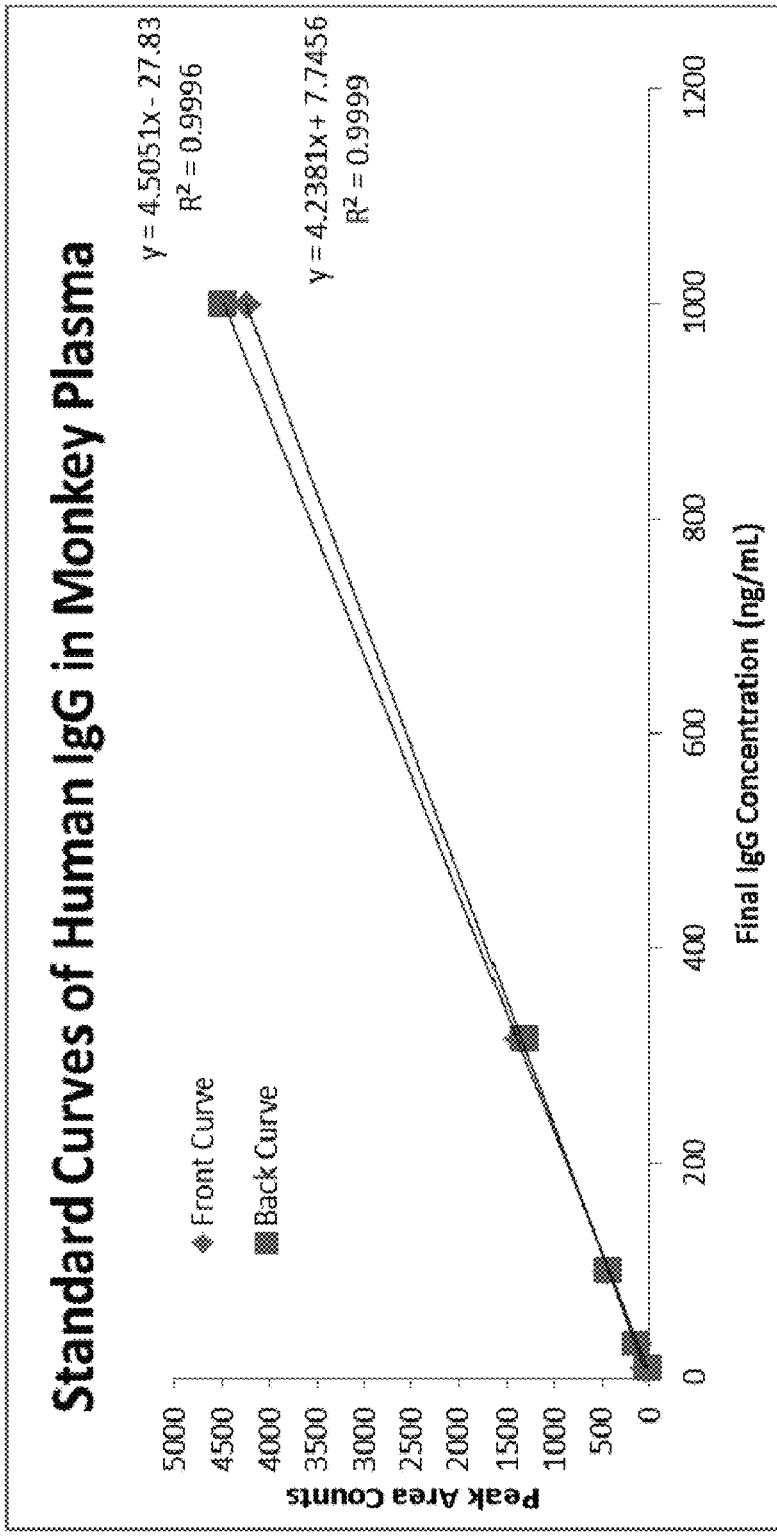
FIG. 21: Standard Curves of Human IgG in Monkey Plasma without pretreatment using immobilized enzyme prepared according to Example 2, packed in a strip of 8 format prepared according to Example 9.

A plot of these results can be seen in FIG. 21

TABLE 31

Replicate analyses of human IgG1 in monkey plasma at
various concentrations

| | IgG in Monkey Plasma Final IgG Concentration (ng/mL) | | |
|---|---|---|---|
| | 10 | 100 | 1000 |
| Sample 1 | 33 | 435 | 4942 |
| Sample 2 | 25 | 416 | 4575 |
| Sample 3 | 22 | 454 | 4989 |
| Sample 4 | 27 | 400 | 4868 |
| Sample 5 | 26 | 440 | 4693 |
| Sample 6 | 17 | 400 | 4547 |
| Sample 7 | 21 | 405 | 4536 |
| Sample 8 | 19 | 391 | 4514 |
| Average | 24 | 418 | 4708 |
| StDev | 5 | 23 | 197 |
| CV (%) | 21.3 | 5.4 | 4.2 |

Example 28: Quantitation of Human IgG in Mouse Plasma

The results below demonstrate quantitation of human IgG in 50 uL mouse plasma diluted in 150 uL of 50 mM TBS, 500 mM CaCl$_2$, 10% glycerol, digestion by immobilized enzyme prepared according to Example 2 that was packed in a strip of 8 format prepared according to Example 9. Digestion occurred in 75 minutes using a ThermoMixer C operated at 70° C.

TABLE 32

Sample preparation and LC/MS parameters for the digestion and analysis of human IgG$_1$ in 50 uL monkey plasma

| Reaction Conditions | |
| --- | --- |
| Equipment | Eppendorf ThermoMixer C |
| Sample | Varying concentrations human IgG in mouse plasma |
| Digest Settings | 70° C., 1600 RPM |
| Time | 75 minutes |
| Digest Buffer | 50 mM TBS, 500 mM CaCl$_2$, 10% glycerol |
| Diluent | 50 mM TBS, 100 mM CaCl$_2$ |
| Digest to Diluent ratio | 1:99 |
| Resin Amount | 15 uL |
| LCMS Conditions Used for Analysis | |
| Injection Volume | 5 uL of diluted sample |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK (SEQ. ID. NO. 5) - 937.74/836.43 |

TABLE 33

Calibration curves of human IgG1 in mouse plasma

| | IgG in Mouse Plasma Final IgG Concentration (ng/mL) | | | | |
| --- | --- | --- | --- | --- | --- |
| | 10 | 31.6 | 100 | 316 | 1000 |
| Peak Areas Front Curve | 40.76 | 163 | 473 | 1709 | 5123 |
| Peak Areas Back Curve | 42.25 | 136 | 438 | 1455 | 4596 |

Figure 22:
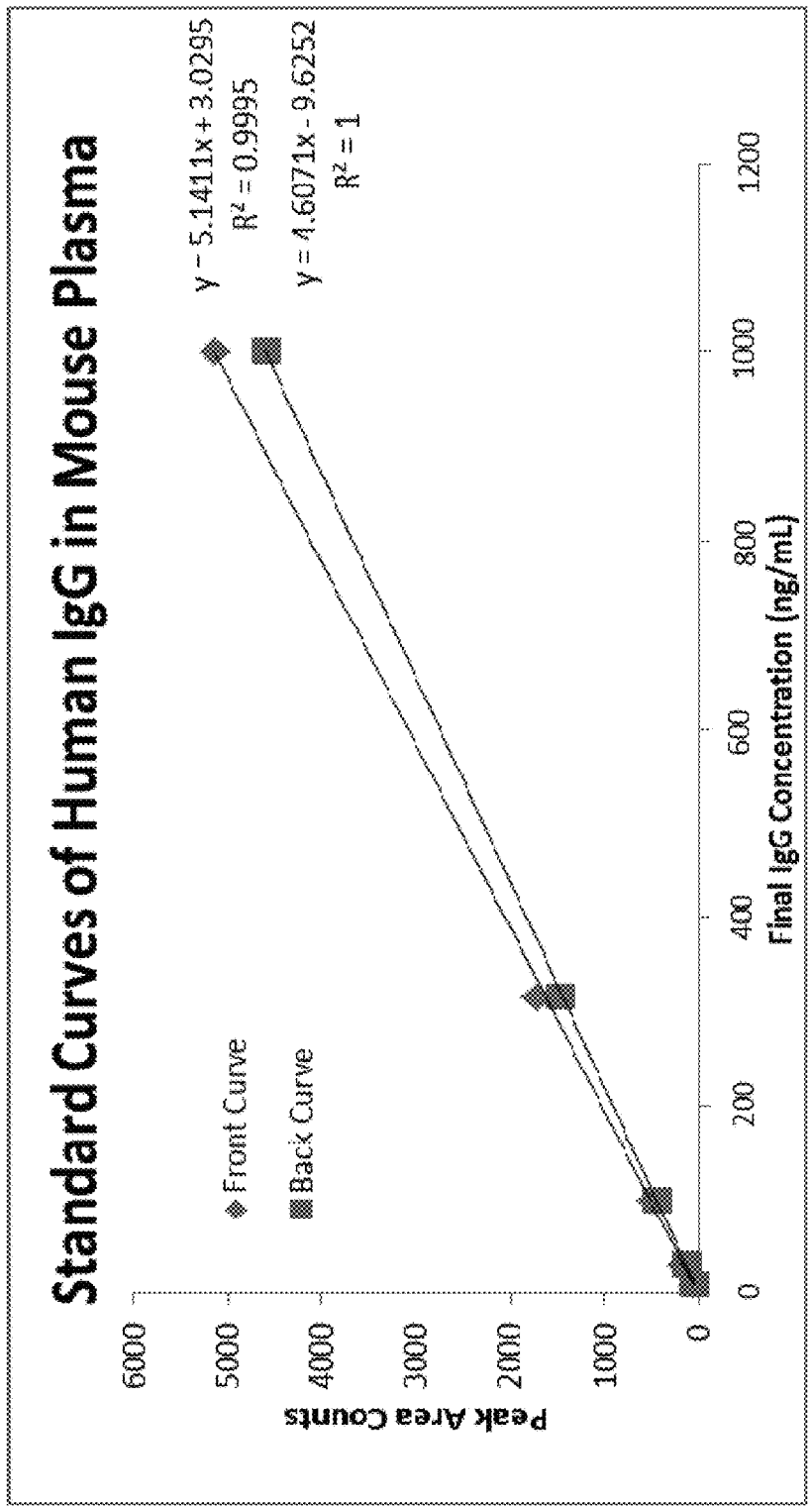
FIG. 22: Standard Curves of Human IgG in Mouse Plasma without pretreatment using immobilized enzyme prepared according to Example 2, packed in a strip of 8 format prepared according to Example 9.

A plot of these results can be seen in FIG. 22

TABLE 34

Replicate analyses of human IgG1 in mouse plasma at various concentrations

| | IgG in Mouse Plasma Final IgG Concentration (ng/mL) | | |
| --- | --- | --- | --- |
| | 10 | 100 | 1000 |
| Sample 1 | 28 | 483 | 5085 |
| Sample 2 | 36 | 483 | 4768 |
| Sample 3 | 28 | 461 | 5363 |
| Sample 4 | 27 | 474 | 4883 |
| Sample 5 | 25 | 462 | 5661 |
| Sample 6 | 32 | 405 | 4911 |
| Sample 7 | 27 | 494 | 5240 |
| Sample 8 | 27 | 517 | 5423 |
| Average | 29 | 472 | 5167 |
| StDev | 4 | 33 | 308 |
| CV (%) | 12.2 | 6.9 | 6 |

Example 29: Quantitation of Human IgG in Beagle Plasma

The results below demonstrate quantitation of human IgG in 50 uL beagle plasma diluted in 150 uL of 50 mM TBS, 500 mM CaCl2, 10% glycerol, digestion by immobilized enzyme prepared according to Example 2 that was packed in a strip of 8 format prepared according to Example 9. Digestion occurred in 75 minutes using a ThermoMixer C operated at 70° C.

TABLE 35

Sample preparation and LC/MS parameters for the digestion and analysis of human IgG$_1$ in 50 uL beagle plasma

| Reaction Conditions | |
| --- | --- |
| Equipment | Eppendorf ThermoMixer C |
| Sample | Varying concentrations human IgG in beagle plasma |
| Digest Settings | 70° C., 1600 RPM |
| Time | 75 minutes |
| Digest Buffer | 50 mM TBS, 500 mM CaCl$_2$, 10% glycerol |
| Diluent | 50 mM TBS, 100 mM CaCl$_2$ |
| Digest to Diluent ratio | 1:99 |
| Resin Amount | 15 uL |
| LCMS Conditions Used for Analysis | |
| Injection Volume | 5 uL of diluted sample |
| Sample | Hu IgG$_1$ |
| Reversed Phase A | 2% ACN (aq) 0.1% Formic Acid |
| Reversed Phase B | 90% ACN (aq) 0.1% Formic Acid |
| Reversed Phase Gradient | 2-70% B in 5 minutes at 500 uL/min |
| Peptide Sequence - MS1/MS2 | TTPPVLDSDGSFFLYSK (SEQ. ID. NO. 5) - 937.74/836.43 |

TABLE 36

Calibration curves of human IgG1 in beagle plasma

| | IgG in Beagle Plasma Final IgG Concentration (ng/mL) | | | | |
| --- | --- | --- | --- | --- | --- |
| | 10 | 31.6 | 100 | 316 | 1000 |
| Peak Areas Front Curve | 92.99 | 323 | 962 | 2934 | 9401 |
| Peak Areas Back Curve | 116 | 272 | 988 | 2981 | 9068 |

Figure 23:
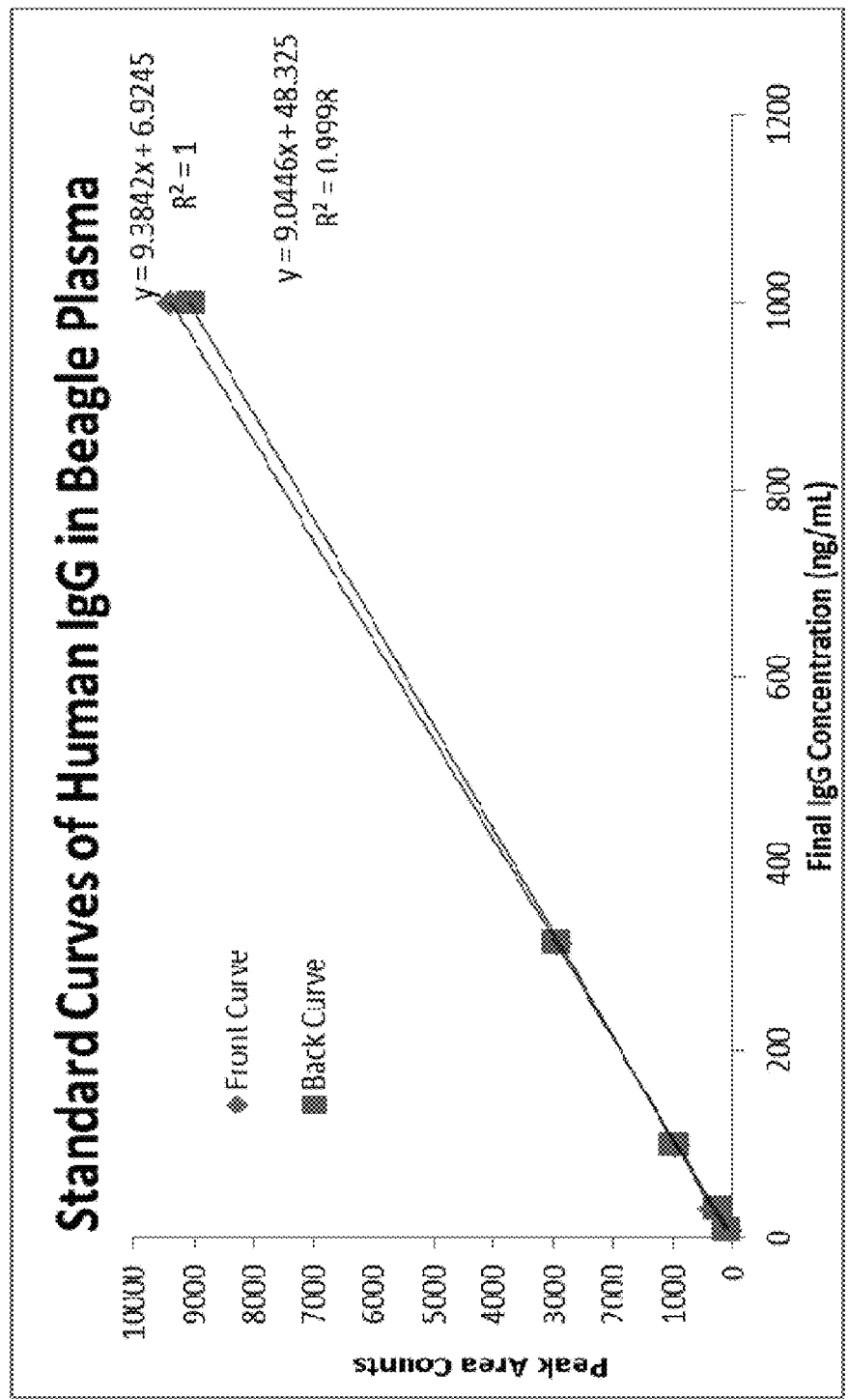
FIG. 23: Standard Curves of IgG in Beagle Plasma without pretreatment using immobilized enzyme prepared according to Example 2, packed in a strip of 8 format prepared according to Example 9.

A plot of these results can be seen in FIG. 23

TABLE 37

Replicate analyses of human IgG1 in beagle plasma at various concentrations

| | IgG in Beagle Plasma Final IgG Concentration (ng/mL) | | |
| --- | --- | --- | --- |
| | 10 | 100 | 1000 |
| Sample 1 | 108 | 917 | 9204 |
| Sample 2 | 92 | 888 | 9565 |
| Sample 3 | 99 | 938 | 9365 |
| Sample 4 | 94 | 957 | 9788 |
| Sample 5 | 73 | 950 | 8903 |
| Sample 6 | 72 | 918 | 9751 |
| Sample 7 | | 914 | 9384 |
| Sample 8 | 90 | 973 | 9746 |
| Average | 90 | 932 | 9463 |
| StDev | 13 | 28 | 311 |
| CV (%) | 14.7 | 3 | 3.3 |

Example 30: Peptide Mapping of Native Proteins without Reduction and Alkylation Human serum albumin was used in this experiment. Since human serum albumin has a large number of disulfide bonds it has historically been considered extremely difficult generate peptides using trypsin without reduction and alkylation. In this study, a Perfinity formulated immobilized enzyme reactor was used to successfully conduct disulfide bond mapping without going through alkylation and reduction processes. 15 uL of slurry prepared as described in Example 2 was added to an eppendorf tube. 6 uL of 50 mg/mL human serum albumin standard was diluted into 994 uL tris-buffered saline. 200 uL of this sample was added to the 15 uL of slurry. This sample was placed in a heater/shaker at 70° C. and the sample shaken at 1400 revolutions per minute for 30 minutes. The sample was removed from the heater/shaker, centrifuged and the digest materials decanted. The digested materials were analyzed according to the parameters set forth in Table 38 below.

TABLE 38

LC/MS Analyses of native Human Serum Albumin Digested
Using the IMER Preparation Described Above

| Sample | Native Human Serum Albumin |
|---|---|
| Injection Volume | 100 uL |
| Reversed Phase A | 2% ACN (aq) 0.1% Formic Acid |
| Reversed Phase B | 90% ACN (aq) 0.1% Formic Acid |
| Reversed Phase Gradient | 0-40% B in 120 minutes at 200 ul/min |
| MS1/MS2 | 200-2000 |
| MS1/MS2 | Nth Order Double Play, Analyzing Top Ten Peaks |
| Dynamic Exclusion Parameters | |
| Repeat Count | 2 |
| Repeat Duration (s) | 6 |
| Exclusion List Size | 500 |
| Exclusion Mass Width | Low: 0.5, High: 1.5 |

The analysis of the mass spectrometric results indicated that peptides corresponding to over 70% of amino acid sequence could be identified.

Sequence of human serum albumin SEQ ID NO: 6

DAHKSEVAHRFKDLGEENFKALVLIAFAQYLQQCPFEDHVKLVNEVTEFA

KTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFY

APELLFFAKRYKAAFTFCCQAADKAACLLPKLDELRDEGKASSAKQRLQK

CASLQKFGERAFKAWAVARLSQRFPKAEFAEVSKLVTDLTKVHTECCHGD

LLECADDRADLAKYICENQDSISSKLKECCEKPLLEKSHCIAEVENDEMP

ADLPSLAADFVESKDVCKNYAEAKDVFLGMFLYEYARRHPDYSVVLLLRL

AKTYETTLEKCCAAADPHECYAKVFDEFKPLVEEPQNLIKQNCELFEQLG

EYKFQNALLVRYTKKVPQVSTPTLVEVSRNLGKVGSKCCKHPEAKRMPCA

EDYLSVVLNQLCVLHEKTPVSDRVTKCCTESLVNRRPCFSALEVDETYVP

KEFNAETFTFHADICTLSEKERQIKKQTALVELVKHKPKATKEQLKAVMD

DFAAFVEKCCKADDKETCFAEEGKKLVAASQAALGL

Human Serum Albumin Coverage as Determined by Thermo Proteome Discoverer Software Sequences Underlined were Positively Identified:

DAHKSEVAHRFKDLGEENFKALVLIAFAQYLQQCPFEDHVKLVNEVTEFA

KTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFY

APELLFFAKRYKAAFTECCQAADKAACLLPKLDELRDEGKASSAKQRLKC

ASLQKFGERAFKAWAVARLSQRFPKAEFAEVSKLVTDLTKVHTECCHGDL

LECADDRADLAKYICENQDSISSKLKECCEKPLLEKSHCIAEVENDEMPA

DLPSLAADFVESKDVCKNYAEAKDVFLGMFLYEYARRHPDYSVVLLLRLA

KTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAE

DYLSVVLNQLCVLHEKTPVSDRVTKCCTESLVNRRPCFSALEVDETYVPK

EFNAETFTFHADICTLSEKERQIKKQTALVELVKHKPKATKEQLKAVMDD

FAAFVEKCCKADDKETCFAEEGKKLVAASQAALGL

Thus, using a Perfinity formulated immobilized enzyme reactor, protein analysis of tough to obtain peptide map becomes possible, especially for those with disulfide bonds or other proteins that require harsh denaturing conditions. The formulation and its process will greatly reduce the time and cost associated with the sample preparation, thus providing a quick assessment of the target protein in relatively economic fashion.

Example 31: Peptide Mapping of Native Proteins with Reduction and Alkylation

Human serum albumin was again used in this experiment. In this study, a Perfinity formulated immobilized enzyme reactor was used to successfully conduct peptide mapping after going through alkylation and reduction process. 15 uL of slurry prepared as described in Example 2 was added to an eppendorf tube. 3 uL of 50 mg/mL human serum albumin standard was diluted into 47 uL tris-buffered saline. 200 uL 6M guanidine-hydrochloride 5 mM dithiothreitol (DTT) was added and the sample incubated for 1 hour at 60° C. After this incubation this sample was allowed to cool to room temperature. 40 uL of 20 mg/mL iodoacetic acid was added and the sample was incubated at room temperature in the dark for 1 hour. Finally, the sample was diluted with an additional 710 uL of tris-buffered saline pH 7.4. 200 uL of this sample was added to the 15 uL of slurry. This sample was placed in a heater/shaker at 40° C. and the sample shaken at 1400 revolutions per minute for 30 minutes. The sample was removed from the heater/shaker, centrifuged and the digest materials decanted. The digested materials were analyzed according to the parameters set forth in Table 39 below.

TABLE 39

LC/MS parameters used for the analyses of reduced and alkylated Human
Serum Albumin digested using the IMER preparation described, above

| Sample | Native Human Serum Albumin |
|---|---|
| Injection Volume | 100 uL |
| Reversed Phase A | 2% ACN (aq) 0.1% Formic Acid |
| Reversed Phase B | 90% ACN (aq) 0.1% Formic Acid |
| Reversed Phase Gradient | 0-40% B in 120 minutes |
| MS1/MS2 | 200-2000 |
| MS1/MS2 | Nth Order Double Play, Analyzing Top Ten Peaks |
| Dynamic Exclusion Parameters | |
| Repeat Count | 2 |
| Repeat Duration (s) | 6 |
| Exclusion List Size | 500 |
| Exclusion Mass Width | Low: 0.5, High: 1.5 |

Human Serum Albumin Coverage as Determined by Thermo Proteome Discoverer Software Sequences Underlined were Positively Identified:

DAHKSEVAHRFKDLGEENFKALVLIAFAQYLQQCPFEDHVKLVNEVTEFA

KTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFY

APELLFFAKRYKAAFTECCQAADKAACLLPKLDELRDEGKASSAKQRLKC

ASLQKFGERAFKAWAVARLSQRFPKAEFAEVSKLVTDLTKVHTECCHGDL

LECADDRADLAKYICENQDSISSKLKECCEKPLLEKSHCIAEVENDEMPA

DLPSLAADFVESKDVCKNYAEAKDVFLGMFLYEYARRHPDYSVVLLLRLA

KTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAE

DYLSVVLNQLCVLHEKTPVSDRVTKCCTESLVNRRPCFSALEVDETYVPK

EFNAETFTFHADICTLSEKERQIKKQTALVELVKHKPKATKEQLKAVMDD

FAAFVEKCCKADDKETCFAEEGKKLVAASQAALGL

It should be understood that the foregoing relates to exemplary embodiments of the disclosure and that modifications may be made without departing from the spirit and scope of the invention as set forth in the following claims.

The invention claimed is:

1. An immobilized enzyme reactor (IMER) preserving optimum enzyme thermal stability and activity at protein denaturing conditions, wherein the IMER comprises the following components:
   a. at least one trypsin enzyme, wherein the trypsin enzyme comprises:
      i) at least one hydrophilic modification to the trypsin enzyme's exterior residues, and
      ii) at least one hydrophobic modification to the trypsin enzyme's interior residues,
      wherein the interior of the trypsin enzyme is made more hydrophobic through the use of a hydrophobic modifier sized to penetrate the enzyme,
      wherein the hydrophobic modifier is an N-hydroxy succinimide, and
      wherein the trypsin enzyme has thermal stability and greater than 50% activity at protein denaturing conditions comprising a temperature ranging from about 60° C. to about 105° C., and
   b. an extended hydrophilic polymer coating immobilizing the trypsin enzyme to a supporting material, wherein the extended hydrophilic polymer coating comprises a molecular weight of at least 2500 g/mol.
2. The IMER of claim 1, wherein the IMER is in the form of a column, an eppendorf tube, a pipette tip, a multi-well plate, or a magnetic bead.
3. The IMER of claim 1, wherein the IMER contains reaction buffer comprised of organic solvents, chaotropes, surfactants, detergents, sugars, salts or any combination thereof.
4. The IMER of claim 1, wherein the supporting material is:
   a) selected from the group consisting of polystyrene, polystyrene/divinylbenzene, silica, controlled porosity glass, dextrans, agarose, acrylates and nitrocellulose,
   b) in the form of a particle, a monolithic, a membrane, a planar or microfluidic channel, and/or
   c) comprising a magnetic core for sample handling in robotic devices.
5. The IMER of claim 1, wherein the protein denaturing conditions comprise a temperature of about 60° C.
6. The IMER of claim 1, wherein the protein denaturing conditions comprise a temperature of about 70° C.
7. The IMER of claim 1, wherein the protein denaturing conditions comprise a temperature of about 75° C.
8. The IMER of claim 1, wherein the protein denaturing conditions comprise a temperature of about 85° C.
9. The IMER of claim 1, wherein the protein denaturing conditions comprise a temperature ranging from about 70° C. to about 105° C.
10. The IMER of claim 1, wherein the extended hydrophilic polymer coating further comprises a hydrophilic polymer selected from the group consisting of polymerized glycidol and polyethylene glycol.
11. The IMER of claim 1, wherein the extended hydrophilic polymer coating comprises at least one hydrophilic modification at multiple sites on the enzyme's exterior residues.
12. The IMER of claim 1, wherein the at least one hydrophilic modification to the enzyme's exterior residue is a complete hydrophilization of the exterior of the enzyme.
13. The IMER of claim 10, wherein the hydrophilic polymer is polyethylene glycol.
14. The IMER of claim 1, wherein the N-hydroxy succinimide is acetic acid N-hydroxy succinimide.
15. The IMER of claim 1, further comprising calcium chloride.
16. The IMER of claim 15, wherein the concentration of calcium chloride is at or above 60 mM.
17. The IMER of claim 15, wherein the trypsin enzyme has thermal stability and greater than 50% activity at protein denaturing conditions comprising a temperature of about 75° C.
18. The IMER of claim 16, wherein the concentration of calcium chloride is about 60 mM.
19. The IMER of claim 16, wherein the concentration of calcium chloride is about 260 mM.
20. The IMER of claim 17, wherein the trypsin enzyme has thermal stability and greater than 50% activity at the protein denaturing conditions after 60 minutes of digestion.
21. The IMER of claim 1, wherein the trypsin enzyme has thermal stability and 100% activity at the protein denaturing conditions.
22. The IMER of claim 20, wherein the trypsin enzyme has thermal stability and 100% activity at the protein denaturing conditions.
23. A method of digesting one or more protein samples using the IMER of claim 1, the method comprising:
   a. mixing the IMER with the one or more protein samples,
   b. heating the IMER and the sample to a temperature ranging from about 60° C. to about 105° C., and
   c. digesting the protein sample,
      wherein the trypsin enzyme is capable of digesting the protein sample without a pretreatment, and
      wherein the pretreatment is selected from the group consisting of alkylation, reduction, and denaturation.
24. The method of claim 23, wherein digesting the protein sample occurs simultaneously with denaturing the protein sample.
25. The method of claim 23, wherein the reaction time for digesting the protein sample is about 6 seconds.
26. The method of claim 23, wherein the reaction time for digesting the protein sample is about 15 seconds.

27. The method of claim 23, wherein the reaction time for digesting the protein sample is about 30-120 seconds.

28. A method of denaturing and digesting one or more protein samples using the IMER of claim 1, the method comprising:
   a. mixing the IMER with the one or more protein samples,
   b. heating the IMER and the sample to a temperature ranging from about 60° C. to about 105° C.,
   c. denaturing the protein sample, and
   d. digesting the protein sample,
      wherein the trypsin enzyme is capable of denaturing and digesting the protein sample without a pretreatment, and
      wherein the pretreatment is selected from the group consisting of alkylation and reduction.

29. The method of claim 28, wherein digesting the protein sample occurs simultaneously with denaturing the protein sample.

30. The method of claim 28, wherein the reaction time for digesting the protein sample is about 6 seconds.

31. The method of claim 28, wherein the reaction time for digesting the protein sample is about 15 seconds.

32. The method of claim 28, wherein the reaction time for digesting the protein sample is about 30-120 seconds.

33. The method of claim 23, further comprising adding calcium chloride to the IMER and the one or more protein samples.

34. The method of claim 33, wherein the concentration of calcium chloride is at or about 60 mM.

35. The method of claim 28, further comprising adding calcium chloride to the IMER and the one or more protein samples.

36. The method of claim 35, wherein the concentration of calcium chloride is at or about 60 mM.

* * * * *